US012722163B2

(12) United States Patent
Kusters

(10) Patent No.: US 12,722,163 B2
(45) Date of Patent: Sep. 1, 2026

(54) INTERFACE DETECTION AND CONTROL USING A PHOTODETECTOR ARRAY

(71) Applicant: Fenwal, Inc., Lake Zurich, IL (US)

(72) Inventor: Benjamin E. Kusters, Pleasant Prairie, WI (US)

(73) Assignee: Fenwal, Inc., Lake Zurich, IL (US)

( * ) Notice: Subject to any disclaimer, the term of this patent is extended or adjusted under 35 U.S.C. 154(b) by 576 days.

(21) Appl. No.: 18/134,629

(22) Filed: Apr. 14, 2023

(65) Prior Publication Data

US 2023/0330686 A1 Oct. 19, 2023

Related U.S. Application Data

(60) Provisional application No. 63/331,959, filed on Apr. 18, 2022.

(51) Int. Cl.
*B04B 13/00* (2006.01)
*B04B 5/04* (2006.01)
(Continued)

(52) U.S. Cl.
CPC ............ *B04B 13/00* (2013.01); *B04B 5/0442* (2013.01); *G01N 21/31* (2013.01); *G01N 33/491* (2013.01);
(Continued)

(58) Field of Classification Search
CPC . B04B 13/00; B04B 5/0442; B04B 2013/006; B04B 11/02; B04B 9/10;
(Continued)

(56) References Cited

U.S. PATENT DOCUMENTS 3,684,450 A 8/1972 Adler et al.
4,567,373 A * 1/1986 O'Meara, Jr. ......... B04B 5/0421 356/427

(Continued)

FOREIGN PATENT DOCUMENTS

EP 1701149 A1 9/2006
EP 2988113 A1 2/2016

(Continued)

OTHER PUBLICATIONS

Extended European Search Report for European Patent Application No. 23167895.4-1113, dated Sep. 11, 2023.

*Primary Examiner* — Claire X Wang
*Assistant Examiner* — Shuyi S. Liu
(74) *Attorney, Agent, or Firm* — Cook Alex Ltd.

(57) ABSTRACT

Systems and methods are provided for determining and controlling the location of an interface between separated fluid components within a channel of a centrifugal separation chamber being rotated about a rotational axis. Light from a light source is received by a collimator, which directs collimated light through the channel in a direction substantially parallel to the rotational axis. At least a portion of the collimated light exiting the channel is received by a light detector configured as a photodetector array. A signal emitted by the light detector is received by a controller, which determines the location of an interface between separated fluid components within the channel based at least in part on the signal. When the controller determines that the interface is not at a target location within the channel, the controller controls a centrifugal separator and/or a pump system to move the interface to the target location.

17 Claims, 12 Drawing Sheets

(51) Int. Cl.

| | |
|---|---|
| ***G01N 21/31*** | (2006.01) |
| ***G01N 33/49*** | (2006.01) |
| *G01N 1/40* | (2006.01) |

(52) U.S. Cl.

CPC .................. *B04B 2013/006* (2013.01); *G01N 2001/4083* (2013.01); *G01N 2201/0633* (2013.01)

(58) Field of Classification Search

CPC ................ G01N 21/31; G01N 33/491; G01N 2001/4083; G01N 2201/0633; A61M 1/3622; A61M 1/36224; A61M 1/362265; A61M 2205/3306; A61M 2205/331; A61M 1/3696; A61M 1/3693; A61M 1/02; A61M 1/029; A61M 1/265; A61M 1/3603; A61M 1/36222; A61M 1/362227; A61M 1/36225; A61M 1/3644; A61M 2205/3365; A61M 2202/0415; A61M 2202/0429; A61M 2205/3334; A61M 2205/50; A61M 1/38; A61M 1/385; B01D 36/045; B01D 63/16

See application file for complete search history.

(56) References Cited

U.S. PATENT DOCUMENTS

| | | | | |
|---|---|---|---|---|
| 5,277,181 | A * | 1/1994 | Mendelson | A61B 5/14551 356/41 |
| 5,316,667 | A | 5/1994 | Brown et al. | |
| 5,351,686 | A | 10/1994 | Steuer et al. | |
| 5,462,416 | A | 10/1995 | Dennehey et al. | |
| 5,868,696 | A | 2/1999 | Giesler et al. | |
| 5,980,760 | A | 11/1999 | Min et al. | |
| 6,312,607 | B1 | 11/2001 | Brown et al. | |
| 6,419,822 | B2 | 7/2002 | Muller et al. | |
| 7,004,727 | B2 | 2/2006 | Kline et al. | |
| 7,011,761 | B2 | 3/2006 | Muller | |
| 7,297,272 | B2 | 11/2007 | Min et al. | |
| 8,075,468 | B2 | 12/2011 | Min et al. | |
| 8,556,793 | B2 | 10/2013 | Foley et al. | |
| 9,164,078 | B2 | 10/2015 | Min et al. | |
| 9,833,557 | B2 | 12/2017 | Thill et al. | |
| 9,895,482 | B2 | 2/2018 | Kusters et al. | |
| 10,890,524 | B2 | 1/2021 | Kusters | |
| 10,928,302 | B2 | 2/2021 | Esteban et al. | |
| 2003/0070969 | A1 | 4/2003 | Muller et al. | |
| 2004/0241736 | A1 | 12/2004 | Hendee et al. | |
| 2005/0036147 | A1 | 2/2005 | Sterling et al. | |
| 2008/0020481 | A1 | 1/2008 | Yamamoto et al. | |
| 2011/0076695 | A1 | 3/2011 | Ohshiro | |
| 2013/0301901 | A1 | 11/2013 | Satish et al. | |
| 2013/0324815 | A1 | 12/2013 | Jian et al. | |
| 2014/0057771 | A1 | 2/2014 | Case et al. | |
| 2014/0128838 | A1 | 5/2014 | Satish et al. | |
| 2015/0219558 | A1 | 8/2015 | Koudelka et al. | |
| 2015/0247791 | A1 | 9/2015 | Koerperick et al. | |
| 2016/0366876 | A1 | 12/2016 | Min et al. | |
| 2018/0188164 | A1 | 7/2018 | Xu et al. | |
| 2021/0096128 | A1 | 4/2021 | Peyser et al. | |

FOREIGN PATENT DOCUMENTS

| | | | | |
|---|---|---|---|---|
| WO | WO 89/03986 | A1 | 5/1989 | |
| WO | WO-9001682 | A1 * | 2/1990 | G01F 23/2921 |
| WO | WO 96/17243 | A1 | 6/1996 | |
| WO | WO-2008021626 | A2 * | 2/2008 | B04B 13/00 |
| WO | WO-2008021633 | A2 * | 2/2008 | G06T 7/181 |
| WO | WO 2016004018 | A1 | 1/2016 | |
| WO | WO 2017048673 | A1 | 3/2017 | |
| WO | WO 2018/053217 | A1 | 3/2018 | |

* cited by examiner

INTERFACE DETECTION AND CONTROL USING A PHOTODETECTOR ARRAY

CROSS-REFERENCE TO RELATED APPLICATIONS

This application claims the benefit of and priority of U.S. Provisional Patent Application Ser. No. 63/331,959, filed Apr. 18, 2022, the contents of which are incorporated by reference herein.

BACKGROUND

Field of the Disclosure

The present disclosure relates to optical monitoring of fluids within a centrifuge. More particularly, the present disclosure relates to detection and control of an interface between separated fluid components within a centrifuge using a photodetector array.

Description of Related Art

A wide variety of fluid processing systems are presently in practice and allow for a fluid to be fractionated or separated into its constituent parts. For example, various blood processing systems make it possible to collect particular blood constituents, rather than whole blood, from a blood source. Typically, in such systems, whole blood is drawn from a blood source, the particular blood component or constituent is separated, removed, and collected, and the remaining blood constituents are returned to the blood source. Removing only particular constituents is advantageous when the blood source is a human donor or patient, because potentially less time is needed for the donor's body to return to pre-donation levels, and donations can be made at more frequent intervals than when whole blood is collected. This increases the overall supply of blood constituents, such as plasma and platelets, made available for transfer and/or therapeutic treatment.

Whole blood is typically separated into its constituents through centrifugation. In continuous processes, this requires that the whole blood be passed through a centrifuge after it is withdrawn from, and before it is returned to, the blood source. To avoid contamination and possible infection (if the blood source is a human donor or patient), the blood is preferably contained within a preassembled, sterile fluid flow circuit or system during the entire centrifugation process. Typical blood processing systems thus include a permanent, reusable module or assembly containing the durable hardware (centrifuge, drive system, pumps, valve actuators, programmable controller, and the like) that controls the processing of the blood and blood components through a disposable, sealed, and sterile flow circuit that includes a centrifugation chamber and is mounted in cooperation on the hardware.

The hardware engages and spins the disposable centrifugation chamber during a blood separation step. As the flow circuit is spun by the centrifuge, the heavier (greater specific gravity) components of the whole blood in the flow circuit, such as red blood cells, move radially outwardly away from the center of rotation toward the outer or "high-G" wall of the centrifugation chamber. The lighter (lower specific gravity) components, such as plasma, migrate toward the inner or "low-G" wall of the centrifuge. Various ones of these components can be selectively removed from the whole blood by providing appropriately located outlet ports in the flow circuit.

Detection and control of the location of the interface between separated fluid components within the centrifugation chamber is important for efficient collection of the separated components. Predicate systems typically apply time-based optical signal measurements for interface detection and control. Such systems may depend on photodetector surface area or the spot size of a laser light source to determine measurement resolution, with both approaches being a function of the amount of time it takes a spot to pass onto and through a fluid layer (e.g., a plasma layer) in the centrifugation chamber. Such systems may also depend heavily on signal amplification and, thus, circuitry time constants that impact the rise and fall time of the signal.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, an interface monitoring assembly is provided for use in combination with a centrifugal separator configured to rotate a centrifugal separation chamber about a rotational axis. The interface monitoring assembly includes a light source configured to emit a light, a light detector configured as a photodetector array, and a collimator positioned between the light source and the light detector. The collimator is configured to receive at least a portion of the light emitted by the light source and direct collimated light through a channel defined by a centrifugal separation chamber in a direction substantially parallel to the rotational axis. The light detector is configured to receive at least a portion of the collimated light exiting the channel of the centrifugal separation chamber in said direction substantially parallel to the rotational axis. The light detector then emits a signal indicative of a position of an interface between separated fluid components within the channel of the centrifugal separation chamber.

In another aspect, a fluid separation device includes a centrifugal separator, a pump system, and a controller. The controller is configured to control the pump system to convey fluid from a fluid source into a channel defined by a centrifugal separation chamber positioned within the centrifugal separator and to control the centrifugal separator to rotate the centrifugal separation chamber about a rotational axis so as separate at least a portion of the fluid in the channel of the centrifugal separation chamber. The centrifugal separator includes an optical monitor assembly comprising a light source configured to emit a light, a light detector configured as a photodetector array, and a collimator positioned between the light source and the light detector. The collimator is configured to receive at least a portion of the light emitted by the light source and direct collimated light through the channel of the centrifugal separation chamber in a direction substantially parallel to the rotational axis. The light detector is configured to receive at least a portion of the collimated light exiting the channel of the centrifugal separation chamber in said direction substantially parallel to the rotational axis. The light detector then emits a signal indicative of a position of an interface between separated fluid components within the channel of the centrifugal separation chamber. The controller is configured to receive the signal from the light detector and determine the position of the interface between the separated fluid components within the channel of the centrifugal separation chamber based at least in part on the signal.

In yet another aspect, a method is provided for separating a fluid. The method includes conveying fluid from a fluid source into a channel defined by a centrifugal separation chamber. The centrifugal separation chamber is rotated about a rotational axis so as separate at least a portion of the fluid in the channel of the centrifugal separation chamber. Light is emitted through a collimator, which directs collimated light through the channel of the centrifugal separation chamber in a direction substantially parallel to the rotational axis. At least a portion of the collimated light exiting the channel of the centrifugal separation chamber in said direction substantially parallel to the rotational axis is received, followed by a signal being emitted. The signal is used to determine the location of an interface between the separated fluid components within the channel of the centrifugal separation chamber.

DESCRIPTION OF THE ILLUSTRATED EMBODIMENTS

Figure 1:
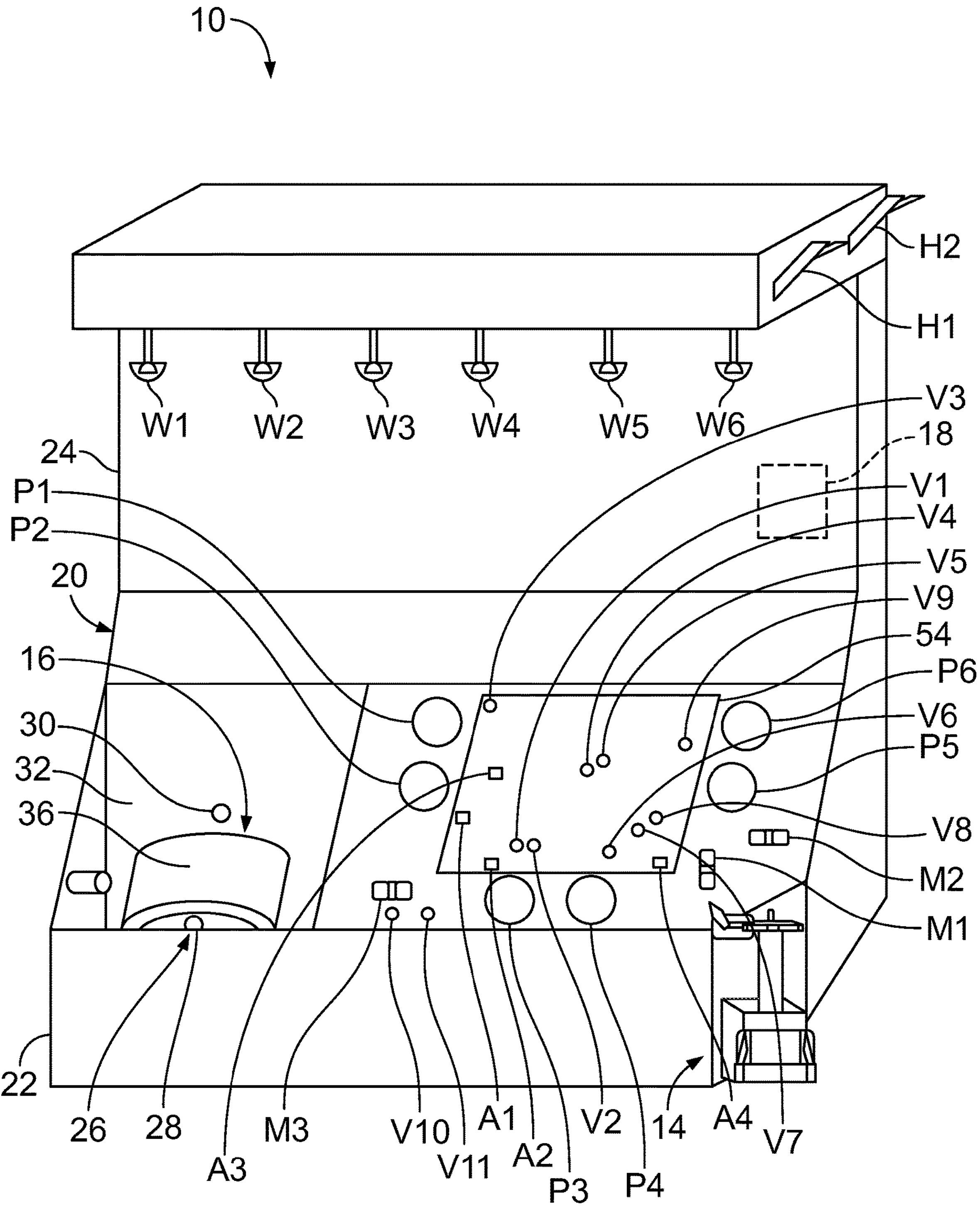
FIG. 1 is a perspective view of an exemplary fluid separation device according to an aspect of the present disclosure.

The embodiments disclosed herein are for the purpose of providing a description of the present subject matter, and it is understood that the subject matter may be embodied in various other forms and combinations not shown in detail. Therefore, specific designs and features disclosed herein are not to be interpreted as limiting the subject matter as defined in the accompanying claims.

FIGS. 1-14 show components of a blood or fluid separation system that embodies various aspects of the present subject matter. Generally speaking, the system includes two principal components, a durable and reusable fluid separation device 10 (FIG. 1) and a disposable fluid flow circuit 12 (FIG. 2). The fluid separation device 10 includes a spinning membrane separator drive unit 14 (FIG. 1), a centrifuge or centrifugal separator 16 (FIG. 3), additional components that control fluid flow through the disposable flow circuit 12, and a controller 18 (FIG. 1), which governs the operation of the other components of the fluid separation device 10 to perform a fluid processing and collection procedure selected by an operator.

I. The Durable Fluid Separation Device

The fluid separation device 10 (FIG. 1) is configured as a durable item that is capable of long-term use. It should be understood that the fluid separation device 10 of FIG. 1 is merely exemplary of one possible configuration and that fluid separation devices according to the present disclosure may be differently configured.

In the illustrated embodiment, the fluid separation device 10 is embodied in a single housing or case 20. The illustrated case 20 includes a generally horizontal portion 22 (which may include an inclined or angled face or upper surface for enhanced visibility and ergonomics) and a generally vertical portion 24. The spinning membrane separator drive unit 14 and the centrifugal separator 16 are shown as being incorporated into the generally horizontal portion 22 of the case 20, while the controller 18 is shown as being incorporated into the generally vertical portion 24. The configuration and operation of the centrifugal separator 16 and selected other components of the fluid separation device 10 will be described in greater detail.

In the illustrated embodiment, the generally horizontal portion 22 is intended to rest on an elevated, generally horizontal support surface (e.g., a countertop or a tabletop), but it is also within the scope of the present disclosure for the case 20 to include a support base to allow the case 20 to be appropriately positioned and oriented when placed onto a floor or ground surface. It is also within the scope of the present disclosure for the case 20 to be mounted to a generally vertical surface (e.g., a wall), by either fixedly or removably securing the generally vertical portion 24 of the case 20 to the surface.

Figure 2:
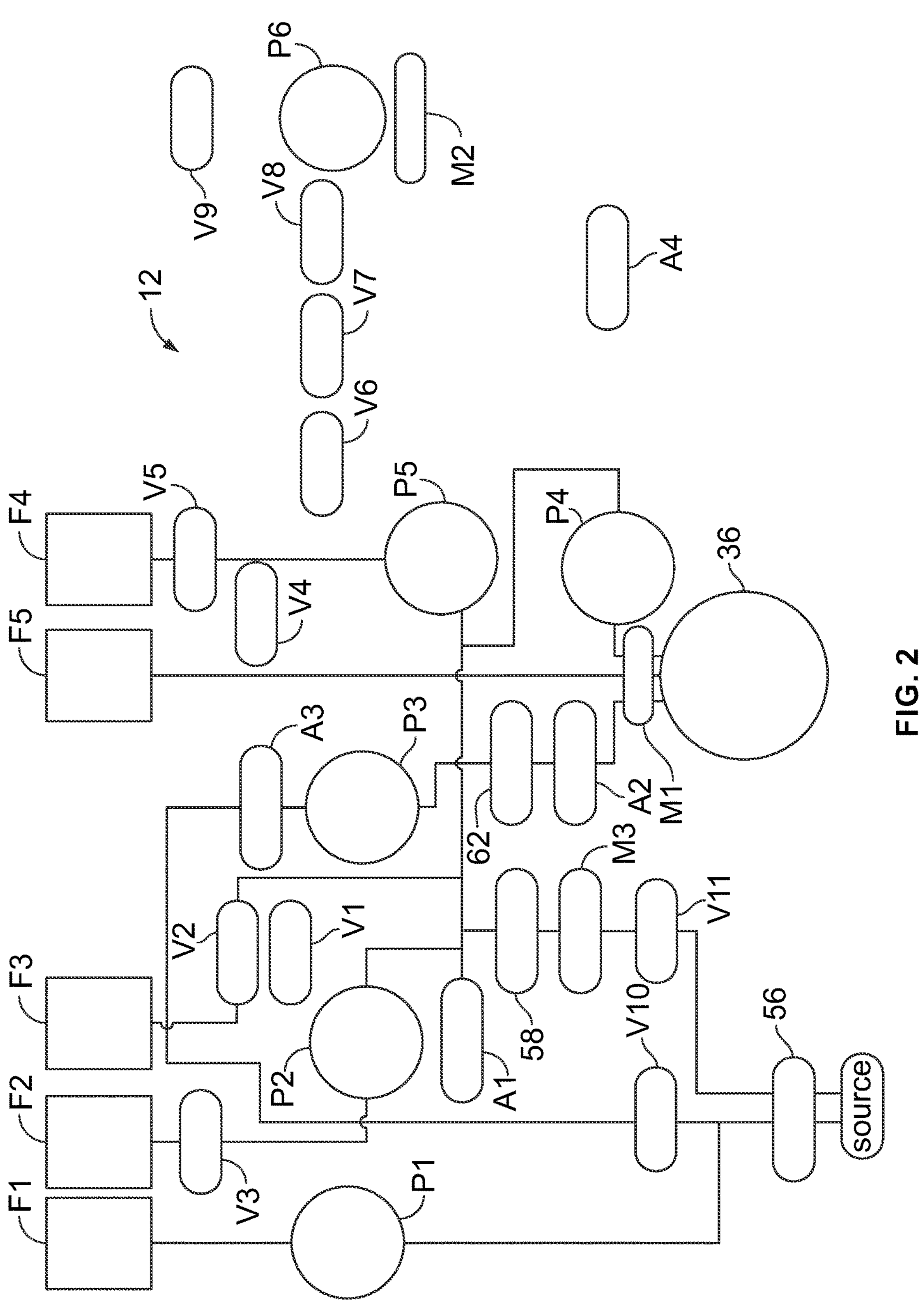
FIG. 2 is a schematic view of a disposable fluid How circuit that may be mounted to the fluid separation device of FIG. 1 to complete a fluid separation system.

The case 20 may be configured to assume only the position or configuration of FIG. 1 or may be configured to move between two or more positions or configurations. For example, in one embodiment, the generally horizontal and vertical portions 22 and 24 are joined by a hinge or pivot, which allows the case 20 to be moved between a functional or open configuration (FIG. 1) in which the generally vertical portion 24 is oriented at approximately 90 degrees to the generally horizontal portion 22 and a transport or closed configuration in which the generally vertical portion 24 is rotated about the hinge to approach the generally horizontal portion 22. In such a reconfigurable embodiment, the generally vertical portion 24 may be considered to be the lid of the case 20, while the generally horizontal portion 22 may be considered to be the base. If the case 20 is so reconfigurable, then it may include a latch for releasably locking the case 20 in its closed configuration and/or a handle, which may be grasped for transporting the case 20 in its closed configuration.

While it may be advantageous for the fluid separation device 10 to be embodied in a compact, portable case 20, it is also within the scope of the present disclosure for the fluid separation device to be embodied in a larger case or fixture that is intended to be installed in a single location and remain in that location for an extended period of time. If the fluid separation device is provided as a fixture, it may be provided with more components and functionality than a more portable version.

A. Centrifugal Separator

Figure 3:
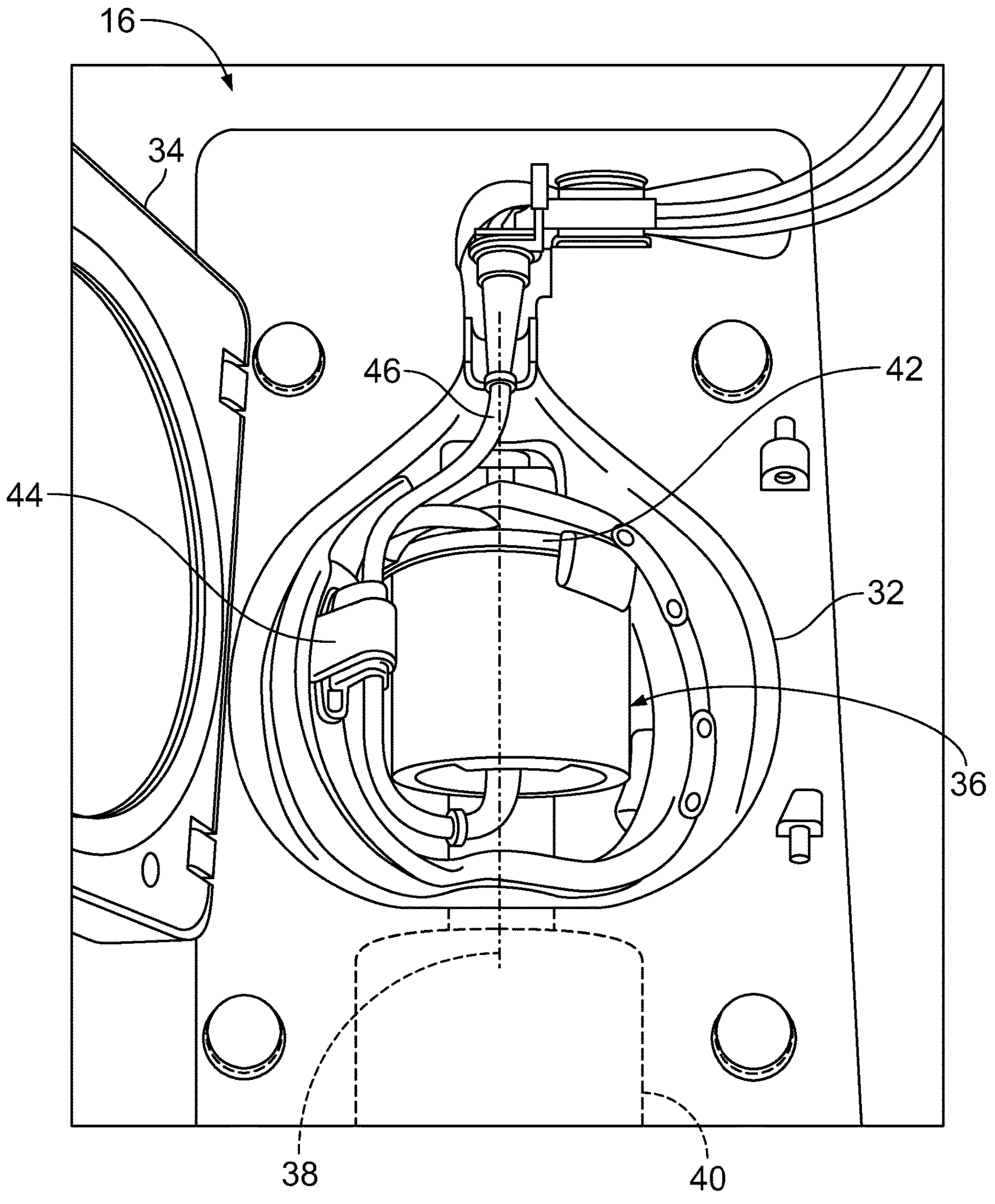
FIG. 3 is a perspective view of an exemplary centrifugal separator of the fluid separation device of FIG. 1, with the centrifugal separation chamber of a fluid flow circuit mounted therein.

The centrifugal separator 16 includes a centrifuge compartment 32 that may receive the other components of the centrifugal separator 16 (FIG. 3). The centrifuge compartment 32 may include a lid 34 that is opened to insert and remove a centrifugal separation chamber 36 of the fluid flow circuit 12. During a separation procedure, the lid 34 may be closed with the centrifugal separation chamber 36 positioned within the centrifuge compartment 32, as the centrifugal separation chamber 36 is spun or rotated about an axis 38 under the power of an electric drive motor or rotor 40 of the centrifugal separator 16.

Figure 4:
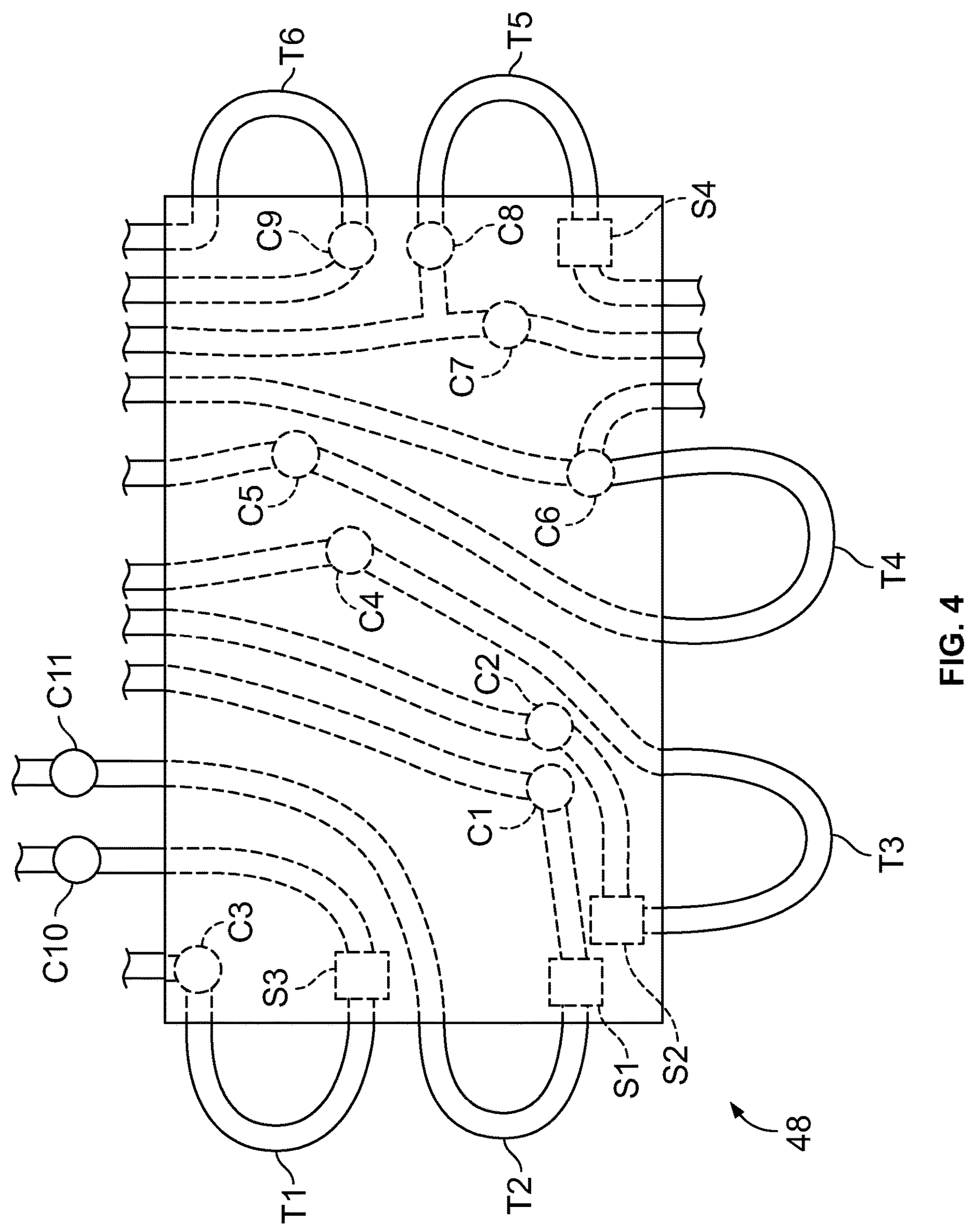
FIG. 4 is a top plan view of an exemplary cassette of a fluid flow circuit, which can be actuated to perform a variety of different fluid processing procedures in association with the fluid separation device shown in FIG. 1.

The particular configuration and operation of the centrifugal separator 16 depends upon the particular configuration of the centrifugal separation chamber 36 of the fluid flow circuit 12. In one embodiment, the centrifugal separator 16 is similar in structure and operation to that of the ALYX® system manufactured by Fenwal, Inc. of Lake Zurich, Illinois, which is an affiliate of Fresenius Kabi AG of Bad Homburg, Germany, as described in greater detail in U.S. Pat. No. 8,075,468, which is incorporated herein by reference. More particularly, the centrifugal separator 16 may include a carriage or support 42 that holds the centrifugal separation chamber 36 and a yoke member 44. The yoke member 44 engages an umbilicus 46 of the fluid flow circuit 12, which extends between the centrifugal separation chamber 36 and a cassette 48 of the fluid flow circuit 12 (FIG. 4). The yoke member 44 causes the umbilicus 46 to orbit around the centrifugal separation chamber 36 at a one omega rotational speed. The umbilicus 46 twists about its own axis as it orbits around the centrifugal separation chamber 36. The twisting of the umbilicus 46 about its axis as it rotates at one omega with the yoke member 44 imparts a two omega rotation to the centrifugal separation chamber 36, according to known design. The relative rotation of the yoke member 44 at a one omega rotational speed and the centrifugal separation chamber 36 at a two omega rotational speed keeps the umbilicus 46 untwisted, avoiding the need for rotating seals.

Fluid is introduced into the centrifugal separation chamber 36 by the umbilicus 46, with the fluid being separated into a layer of less dense components (such as platelet-rich plasma, in the case of whole blood separation) and a layer of more dense components (such as packed red blood cells, in the case of whole blood separation) within the centrifugal separation chamber 36 as a result of centrifugal forces as it rotates.

Components of an interface monitoring assembly 26 (which will be described in greater detail herein) may be positioned within the centrifuge compartment 32 to oversee separation of fluid within the centrifugal separation chamber 36. As shown in FIG. 1, the interface monitoring assembly 26 may include a light source 28 and a light detector 30, which is positioned and oriented to receive at least a portion of the light emitted by the light source 28. The light source 28 emits a light beam through the separated fluid components within the centrifugal separation chamber 36 (which may be formed of a material that substantially transmits the light or at least a particular wavelength of the light without absorbing it). A portion of the light reaches the light detector 30, which transmits a signal to the controller 18 that is indicative of the location of an interface between the separated fluid components. If the controller 18 determines that the interface is not at a target location (which can affect the separation efficiency of the centrifugal separator 16 and/or the quality of the separated fluid components), then it can issue commands to the appropriate components of the fluid separation device 10 to modify their operation so as to move the interface to the proper location.

B. Other Components of the Fluid Separation Device

In addition to the spinning membrane separator drive unit 14 and the centrifugal separator 16, the fluid separation device 10 may include other components compactly arranged to aid fluid processing.

The generally horizontal portion 22 of the case 20 of the illustrated fluid separation device 10 includes a cassette station 54, which accommodates a cassette 48 of the fluid flow circuit 12 (FIG. 4). In one embodiment, the cassette station 54 is similarly configured to the cassette station of U.S. Pat. No. 5,868,696 (which is incorporated herein by reference), but is adapted to include additional components and functionality. The illustrated cassette station 54 includes a plurality of clamps or valves V1-V9 (FIG. 1), which move between a plurality of positions (e.g., between a retracted or lowered position and an actuated or raised position) to selectively contact or otherwise interact with corresponding valve stations C1-C9 of the cassette 48 of the fluid flow circuit 12 (FIG. 4). Depending on the configuration of the fluid flow circuit 12, its cassette 48 may not include a valve station C1-C9 for each valve V1-V9 of the cassette station 54, in which case fewer than all of the valves V1-V9 will be used in a separation procedure.

In the actuated position, a valve V1-V9 engages the associated valve station C1-C9 to prevent fluid flow through that valve station C1-C9 (e.g., by closing one or more ports associated with the valve station C1-C9, thereby preventing fluid flow through that port or ports). In the retracted position, a valve V1-V9 is disengaged from the associated valve station C1-C9 (or less forcefully contacts the associated valve station C1-C9 than when in the actuated position) to allow fluid flow through that valve station C1-C9 (e.g., by opening one or more ports associated with the valve station C1-C9, thereby allowing fluid flow through that port or ports). Additional clamps or valves V10 and V11 may be positioned outside of the cassette station 54 to interact with portions or valve stations C10 and C11 (which may be lengths of tubing) of the fluid flow circuit 12 to selectively allow and prevent fluid flow therethrough. The valves V1-V9 and corresponding valve stations C1-C9 of the cassette station 54 and cassette 48 may be differently configured and operate differently from the valves V10 and V11 and valve stations C10 and C11 that are spaced away from the cassette station 54.

The cassette station 54 may be provided with additional components, such as pressure sensors A1-A4, which interact with sensor stations S1-S4 of the cassette 48 to monitor the pressure at various locations of the fluid flow circuit 12. For example, if the blood source is a human patient, one or more of the pressure sensors A1-A4 may be configured to monitor the pressure of the patient's vein during blood draw and return. Other pressure sensors A1-A4 may monitor the pressure of a spinning membrane separator received by the spinning membrane separator drive unit 14 and a centrifugal separation chamber 36 received by the centrifugal separator 16. The controller 18 may receive signals from the pressure sensor A1-A4 that are indicative of the pressure within the fluid flow circuit 12 and, if a signal indicates a low- or high-pressure condition, the controller 18 may initiate an alarm or error condition to alert an operator to the condition and/or to attempt to bring the pressure to an acceptable level without operator intervention.

The fluid separation device 10 may also include a plurality of pumps R1-P6 (which may be collectively referred to as a pump assembly or pump system) cause fluid to flow through the fluid flow circuit 12. The pumps P1-P6 may be differently or similarly configured and/or function similarly or differently from each other. In the illustrated embodiment, the pumps P1-P6 are configured as peristaltic pumps, which may be generally configured as described in U.S. Pat. No. 5,868,696. Each pump P1-P6 engages a different tubing loop T1-T6 extending from a side surface of the cassette 48 (FIG. 4) and may be selectively operated under command of the controller 18 to cause fluid to flow through a portion of the fluid flow circuit 12. In one embodiment, all or a portion of the cassette station 54 may be capable of translational motion in and out of the case 20 to allow for automatic loading of the tubing loops T1-T6 into the associated pump P1-P6.

The illustrated fluid separation device 10 also includes a centrifugal separator sensor M1 for determining one or more properties of fluids flowing out of and/or into the centrifugal separator 16. If the fluid flowing out of the centrifugal separator 16 includes red blood cells, the centrifugal separator sensor M1 may be configured to determine the hematocrit of the fluid. If the fluid flowing out of the centrifugal separator 16 is platelet-rich plasma, the centrifugal separator sensor M1 may be configured to determine the platelet concentration of the platelet-rich plasma. The centrifugal separator sensor M1 may detect the one or more properties of a fluid by optically monitoring the fluid as it flows through tubing of the fluid flow circuit 12 or by any other suitable approach. The controller 18 may receive signals from the centrifugal separator sensor M1 that are indicative of the one or more properties of fluid flowing out of the centrifugal separator 16 and use the signals to optimize the separation procedure based upon that property or properties. If the property or properties is/are outside of an acceptable range, then the controller 18 may initiate an alarm or error condition to alert an operator to the condition. A suitable device and method for monitoring hematocrit and/or platelet concentration is described in U.S. Pat. No. 6,419,822 (which is incorporated herein by reference), but it should be understood that a different approach may also be employed for monitoring hematocrit and/or platelet concentration of fluid flowing out of the centrifugal separator 16.

The illustrated fluid separation device 10 further includes a spinner outlet sensor M2, which accommodates tubing of the fluid flow circuit 12 that flows a separated substance out of a spinning membrane separator received by the spinning membrane separator drive unit 14. The spinner outlet sensor M2 monitors the substance to determine one or more properties of the substance, and may do so by optically monitoring the substance as it flows through the tubing or by any other suitable approach. In one embodiment, separated plasma flows through the tubing, in which case the spinner outlet sensor M2 may be configured to determine the amount of cellular blood components in the plasma and/or whether the plasma is hemolytic and/or lipemic. This may be done using an optical monitor of the type described in U.S. Pat. No. 8,556,793 (which is incorporated herein by reference) or by any other suitable device and/or method.

The illustrated fluid separation device 10 also includes an air detector M3 (e.g., an ultrasonic bubble detector), which accommodates tubing of the fluid flow circuit 12 that flows fluid to a recipient. It may be advantageous to prevent air from reaching the recipient, so the air detector M3 may transmit signals to the controller 18 that are indicative of the presence or absence of air in the tubing. If the signal is indicative of air being present in the tubing, the controller 18 may initiate an alarm or error condition to alert an operator to the condition and/or to take corrective action to prevent the air from reaching the recipient (e.g., by reversing the flow of fluid through the tubing or diverting flow to a vent location).

The generally vertical portion 24 of the case 18 may include a plurality of weight scales W1-W6 (six are shown, but more or fewer may be provided), each of which may support one or more fluid containers F1-F5 of the fluid flow circuit 12 (FIG. 2). The containers F1-F5 receive fluid components or waste products separated during processing or intravenous fluids or additive fluids. Each weight scale W1-W6 transmits to the controller 18 a signal that is indicative of the weight of the fluid within the associated container F1-F5 to track the change of weight during the course of a procedure. This allows the controller 18 to process the incremental weight changes to derive fluid processing volumes and flow rates and subsequently generate signals to control processing events based, at least in part, upon the derived processing volumes. For example, the controller 18 may diagnose leaks and obstructions in the fluid flow circuit 12 and alert an operator.

The illustrated case 20 is also provided with a plurality of hooks or supports H1 and H2 that may support various components of the fluid flow circuit 12 or other suitably sized and configured objects.

C. Controller

According to an aspect of the present disclosure, the fluid separation device 10 includes a controller 18, which is suitably configured and/or programmed to control operation of the fluid separation device 10. In one embodiment, the controller 18 comprises a main processing unit (MPU), which can comprise, e.g., a Pentium™ type microprocessor made by Intel Corporation, although other types of conventional microprocessors can be used. In one embodiment, the controller 18 may be mounted inside the generally vertical portion 24 of the case 20, adjacent to or incorporated into an operator interface station (e.g., a touchscreen). In other embodiments, the controller 18 and operator interface station may be associated with the generally horizontal portion 22 or may be incorporated into a separate device that is connected (either physically, by a cable or the like, or wirelessly) to the fluid separation device 10.

The controller 18 is configured and/or programmed to execute at least one fluid processing application but, more advantageously, is configured and/or programmed to execute a variety of different fluid processing applications. For example, the controller 18 may be configured and/or programmed to carry out a therapeutic red blood cell exchange procedure and/or a therapeutic plasma exchange procedure. Additional or alternative procedure applications may be included without departing from the scope of the present disclosure.

More particularly, in carrying out any one of these fluid processing applications, the controller 18 is configured and/or programmed to control one or more of the following tasks: drawing fluid into a fluid flow circuit 12 mounted to the fluid separation device 10, conveying fluid through the fluid flow circuit 12 to a location for separation (i.e., into a spinning membrane separator or centrifugal separation chamber 36 of the fluid flow circuit 12), separating the fluid into two or more components as desired, and conveying the separated components into a storage container or to a recipient (which may be the source from which the fluid was originally drawn).

This may include instructing the spinning membrane separator drive unit 14 or the centrifugal separator 16 to operate at a particular rotational speed and instructing a pump P1-P6 to convey fluid through a portion of the fluid flow circuit 12 at a particular flow rate. Hence, while it may be described herein that a particular component of the fluid separation device 10 (e.g., the spinning membrane separator drive unit 14 or the centrifugal separator 16) performs a particular function, it should be understood that that component is being controlled by the controller 18 to perform that function.

Before, during, and after a procedure, the controller 18 may receive signals from various components of the fluid separation device 10 (e.g., the pressure sensors A1-A4) to monitor various aspects of the operation of the fluid separation device 10 and characteristics of the fluid and separated fluid components as they flow through the fluid flow circuit 12. If the operation of any of the components and/or one or more characteristics of the fluid or separated fluid components is outside of an acceptable range, then the controller 18 may initiate an alarm or error condition to alert the operator and/or take action to attempt to correct the condition. The appropriate corrective action will depend upon the particular error condition and may include action that is carried out with or without the involvement of an operator.

For example, the controller 18 may include an interface control module, which receives signals from the light detector 30 of the interface monitoring assembly 26. The signals that the controller 18 receives from the light detector 30 are indicative of the location of an interface between the separated fluid components within the centrifugal separation chamber 36. If the controller 18 determines that the interface is not at a target location, then it can issue commands to the appropriate components of the fluid separation device 10 to modify their operation so as to move the interface to the proper location. For example, the controller 18 may instruct one of the pumps P1-P6 to cause fluid to flow into the centrifugal separation chamber 36 at a different rate and/or for a separated fluid component to be removed from the centrifugal separation chamber 36 at a different rate and/or for the centrifugal separation chamber 36 to be spun at a different speed by the centrifugal separator 16. A particular protocol carried out by the interface control module in adjusting the position of the interface within the centrifugal separation chamber 36 will be described in greater detail.

If provided, an operator interface station associated with the controller 18 allows the operator to view on a screen or display (in alpha-numeric format and/or as graphical images) information regarding the operation of the system. The operator interface station also allows the operator to select applications to be executed by the controller 18, as well as to change certain functions and performance criteria of the system. If configured as a touchscreen, the screen of the operator interface station can receive input from an operator via touch-activation. Otherwise, if the screen is not a touchscreen, then the operator interface station may receive input from an operator via a separate input device, such as a computer mouse or keyboard. It is also within the scope of the present disclosure for the operator interface station to receive input from both a touchscreen and a separate input device, such as a keypad.

II. The Disposable Fluid Flow Circuit

A. Overview

As for the fluid flow circuit or flow set 12 (FIG. 2), it is intended to be a sterile, single use, disposable item. Before beginning a given fluid separation procedure, the operator loads various components of the fluid flow circuit 12 in the case 20 in association with the fluid separation device 10. The controller 18 implements the procedure based upon preset protocols, taking into account other input from the operator. Upon completing the procedure, the operator removes the fluid flow circuit 12 from association with the fluid separation device 10. The portions of the fluid flow circuit 12 holding the collected fluid component or components (e.g., collection containers or bags) are removed from the case 20 and retained for storage, transfusion, or further processing. The remainder of the fluid flow circuit 12 is removed from the case 20 and discarded.

Figure 5:
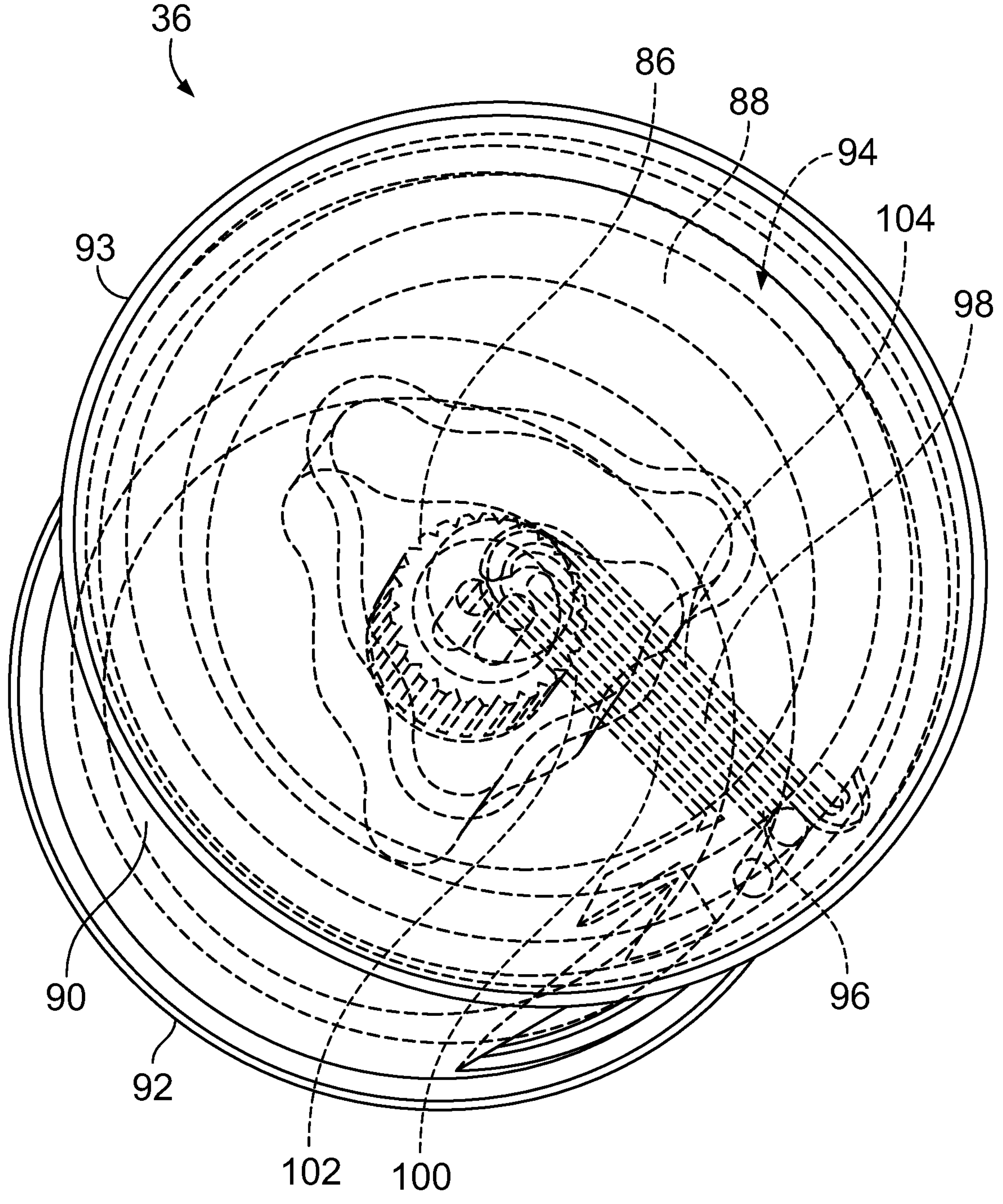
FIG. 5 is a perspective view of an exemplary centrifugal separation chamber of a fluid flow circuit.
Figure 6:
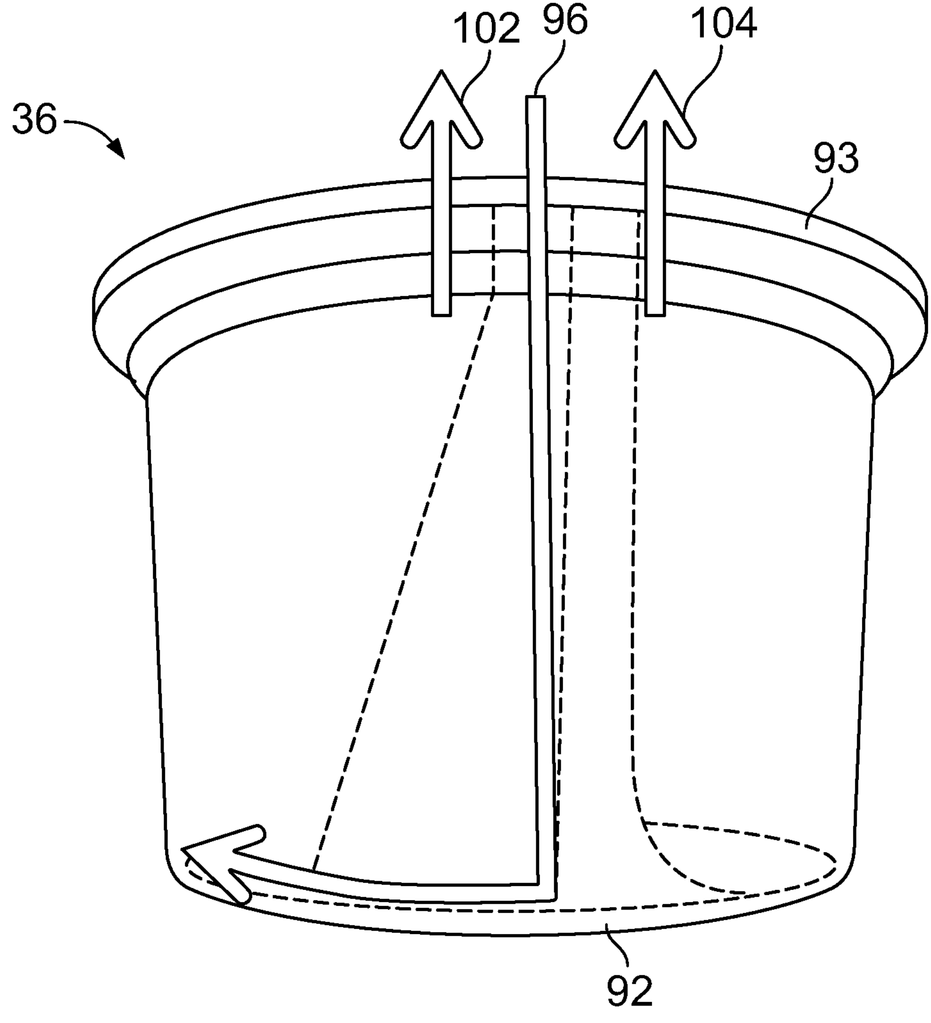
FIG. 6 is a front elevational view of the centrifugal separation chamber of FIG. 5.

A variety of different disposable fluid flow circuits may be used in combination with the fluid separation device 10, with the appropriate fluid flow circuit depending on the separation procedure to be carried out using the system. Generally speaking, though, the fluid flow circuit 12 includes a cassette 48 (FIG. 4), to which the other components of the fluid flow circuit 12 are connected by flexible tubing. The other components may include a plurality of fluid containers F1-F5 (for holding blood, a separated blood component, an intravenous fluid, or an additive solution, for example), one or more fluid source access devices (e.g., a connector for accessing blood within a fluid container), and a spinning membrane separator and/or a centrifugal separation chamber 36 (FIGS. 5 and 6).

B. Cassette and Tubing

The cassette 48 (FIG. 4) provides a centralized, programmable, integrated platform for all the pumping and many of the valving functions required for a given fluid processing procedure. In one embodiment, the cassette 48 is similarly configured to the cassette of U.S. Pat. No. 5,868,696, but is adapted to include additional components (e.g., more tubing loops T1-T6) and functionality.

In use, the cassette 48 is mounted to the cassette station 54 of the fluid separation device 10, with a flexible diaphragm of the cassette 48 placed into contact with the cassette station 54. The flexible diaphragm overlays an array of interior cavities formed by the body of the cassette 48. The different interior cavities define sensor stations S1-S4, valve stations C1-C9, and a plurality of flow paths. The side of the cassette 48 opposite the flexible diaphragm may be sealed by another flexible diaphragm or a rigid cover, thereby sealing fluid flow through the cassette 48 from the outside environment.

Each sensor station S1-S4 is aligned with an associated pressure sensor A1-A4 of the cassette station 54, with each pressure sensor A1-A4 capable of monitoring the pressure within the associated sensor station S1-S4. Each valve station C1-C9 is aligned with an associated valve V1-V9, and may define one or more ports that allow fluid communication between the valve station C1-C9 and another interior cavity of the cassette 48 (e.g., a flow path), As described above, each valve V1-V9 is movable under command of the controller 18 to move between a plurality of positions (e.g., between a retracted or lowered position and an actuated or raised position) to selectively contact the valve stations C1-C9 of the cassette 48. In the actuated position, a valve V1-V9 engages the associated valve station C1-C9 to close one or more of its ports to prevent fluid flow therethrough. In the retracted position, a valve V1-V9 is disengaged from the associated valve station C1-C9 (or less forcefully contacts the associated valve station C1-C9 than when in the actuated position) to open one or more ports associated with the valve station C1-C9, thereby allowing fluid flow therethrough.

As described, a plurality of tubing loops T1-T6 extend from the side surface of the cassette 48 to interact with pumps P1-P6 of the fluid separation device 10. In the illustrated embodiment, six tubing loops T1-T6 extend from the cassette 48 to be received by a different one of six pumps P1-P6, but in other embodiments, a procedure may not require use of all of the pumps P1-P6, in which case the cassette 48 may include fewer than six tubing loops. The different pumps P1-P6 may interact with the tubing loops T1-T6 of the cassette 48 to perform different tasks during a separation procedure. Certain procedures require fewer than all of the sensor stations, valve stations, and/or tubing loops illustrated in the exemplary cassette 48 of FIG. 4, such that it should be understood that the cassettes of different fluid flow circuits 12 may be differently configured (e.g., with fewer sensor stations, valve stations, and/or tubing loops) without departing from the scope of the present disclosure.

Additional tubing extends from the side surface of the cassette 48 to connect to the other components of the fluid flow circuit 12, such as the various fluid containers F1-F5, a spinning membrane separator, and the centrifugal separation chamber 36. If the fluid flow circuit 12 includes a centrifugal separation chamber 36, then the tubing connected to it (which includes one inlet tube and two outlet tubes) may be aggregated into an umbilicus 46 (FIG. 3) that is engaged by the yoke member 44 of the centrifugal separator 16 (as described above) to cause the umbilicus 46 to orbit around and spin or rotate the centrifugal separation chamber 36 during a separation procedure.

Various additional components may be incorporated into the tubing leading out of the cassette 48 or into one of the cavities of the cassette 48. For example, as shown in FIG. 2, a manual clamp 56 may be associated with a line or lines leading to the fluid source and/or fluid recipient, a return line filter 58 (e.g., a microaggregate filter) may be associated with a line leading to a fluid recipient, filters may be positioned upstream of one or more of the fluid containers to remove a substance (e.g., leukocytes) from a separated component (e.g., red blood cells) flowing into the fluid container, and/or an air trap 62 may be positioned on a line upstream of the centrifugal separation chamber 36.

C. Centrifugal Separation Chamber

The fluid flow circuit 12 is provided with a centrifugal separation chamber 36, with FIGS. 5 and 6 illustrating an exemplary centrifugal separation chamber 36. In the illustrated embodiment, the body of the centrifugal separation chamber 36 is preformed in a desired shape and configuration (e.g., by injection molding) from a rigid, biocompatible plastic material, such as a non-plasticized medical grade acrylonitrile-butadiene-styrene (ABS), All contours, ports, channels, and walls that affect the fluid separation process are preformed in a single, injection molded operation. Alternatively, the centrifugal separation chamber 36 can be formed by separate molded parts, either by nesting cup-shaped subassemblies or two symmetric halves.

The underside of the centrifugal separation chamber 36 includes a shaped receptacle 86 (FIG. 5) that is suitable for receiving an end of the umbilicus 46 of the fluid flow circuit 12 (FIG. 3). A suitable receptacle 86 and the manner in which the umbilicus 46 may cooperate with the receptacle 86 to deliver fluid to and remove fluid from the centrifugal separation chamber 36 are described in greater detail in U.S. Pat. No. 8,075,468.

The illustrated centrifugal separation chamber 36 has radially spaced apart inner (low-g) and outer (high-g) side wall portions 88 and 90, a bottom or first end wall portion 92, and a cover or second end wall portion 93. The cover 93 comprises a simple flat part that can be easily welded or otherwise secured to the body of the centrifugal separation chamber 36, Because all features that affect the separation process are incorporated into one injection molded component, any tolerance differences between the cover 93 and the body of the centrifugal separation chamber 36 will not affect the separation efficiencies of the centrifugal separation chamber 36. The wall portions 88 and 90, the bottom 92, and the cover 93 together define an enclosed, generally annular channel 94 (FIG. 5).

The (whole blood) inlet 96 communicating with the channel 94 is defined between opposing interior radial walls 98 and 100. One of the interior walls 98 joins the outer (high-g) wall portion 90 and separates the upstream and downstream ends of the channel 94. The interior walls 98 and 100 define the inlet passageway 96 of the centrifugal separation chamber 36 which, in one flow configuration, allows fluid to flow from the umbilicus 46 to the upstream end of the channel 94.

The illustrated centrifugal separation chamber 36 further includes first and second outlets 102 and 104, respectively, which may be defined by opposing surfaces of interior radial walls. Both the first and second outlets 102 and 104 extend radially inward from the channel 94. The first (plasma) outlet 102 extends radially inward from an opening which, in the illustrated embodiment, is located at the inner side wall portion 88, while the second (red blood cell) outlet 104 extends radially inward from an opening that is associated with the outer side wall portion 90. The illustrated first outlet 102 is positioned adjacent to the inlet 96 (near the upstream end of the channel 94), while the second outlet 104 may be positioned at the opposite, downstream end of the channel 94.

It should be understood that the centrifugal separation chamber 36 illustrated in FIGS. 5 and 6 is merely exemplary and that the centrifugal separation chamber 36 may be differently configured without departing from the scope of the present disclosure.

1. Centrifugal Separation and Interface Detection Principles

As described above, the centrifugal separation chamber 36 may be used to separate any suitable fluid. However, for illustrative purposes, separation of blood will be described herein, as the fluid separation system may be particularly advantageous for blood separation.

Blood flowed into the channel 94 separates into an optically dense layer RBC and a less optically dense layer PLS (FIGS. 7-9) as the centrifugal separation chamber 36 is rotated about the rotational axis 38. The optically dense layer RBC forms as larger and/or heavier blood particles move under the influence of centrifugal force toward the outer (high-g) wall portion 90. The optically dense layer RBC will typically include red blood cells (and, hence, may be referred to herein as the "ABC layer") but, depending on the speed at which the centrifugal separation chamber 36 is rotated, other cellular components (e.g., larger white blood cells) may also be present in the optically dense layer ABC.

The less optically dense layer PLS typically includes a plasma constituent, such as platelet-rich plasma (and, hence, may be referred to herein as the "PLS layer"). Depending on the speed at which the centrifugal separation chamber 36 is rotated and the length of time that the blood is resident therein, other components (e.g., smaller white blood cells and anticoagulant) may also be present in the less optically dense layer PLS.

In one embodiment, blood introduced into the channel 94 via the inlet 96 will travel in a generally clockwise direction (in the orientation of FIG. 5) as the optically dense layer ABC separates from the less optically dense layer PLS. The optically dense layer RBC continues moving in the clockwise direction as it travels the length of the channel 94 along the outer side wall portion 90, from the upstream end to the downstream end, where it exits the channel 94 via the second outlet 104. The less optically dense layer PLS separated from the optically dense layer RBC reverses direction, moving counterclockwise along the inner side wall portion 88 to the first outlet 102, adjacent to the inlet 96. The inner side wall portion 88 may be tapered inward as it approaches the second outlet 104 to force the plasma liberated at or adjacent to the downstream end of the channel 94 to drag the interface back towards the upstream end of the channel 94, where the lower surface hematocrit will re-suspend any platelets settled on the interface.

Figure 7:
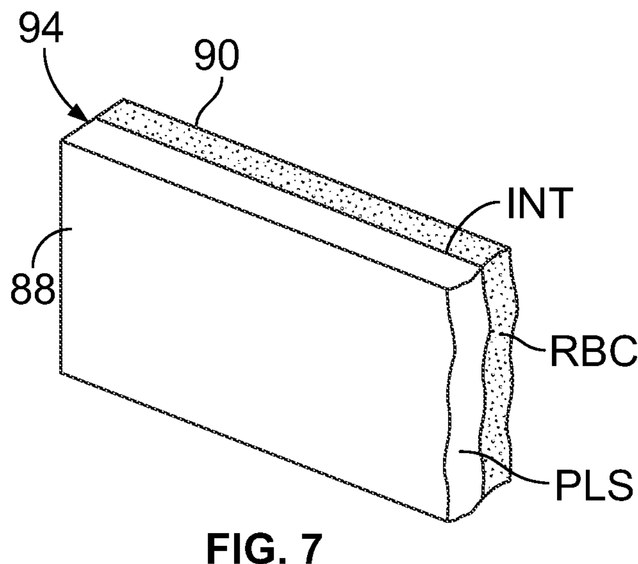
FIG. 7 is an enlarged perspective view of a portion of a channel of the centrifugal separation chamber of FIGS. 5 and 6, with an interface between separated fluid components being positioned at a desired or target location within the channel.
Figure 8:
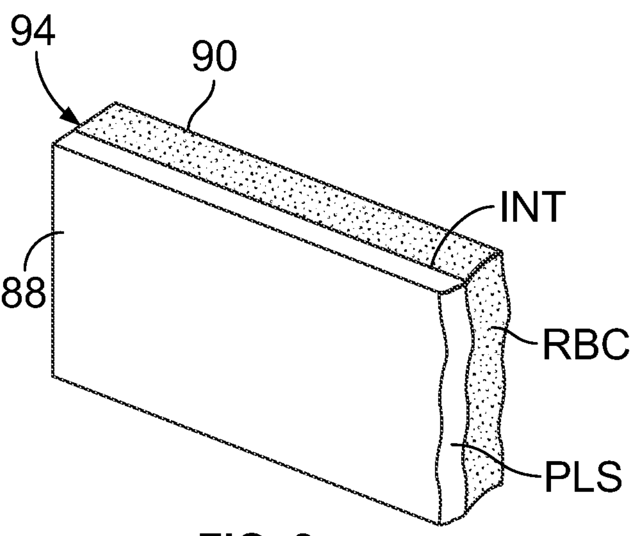
FIG. 8 is an enlarged perspective view of the channel of FIG. 7, with the interface being at an undesired high location within the channel.
Figure 9:
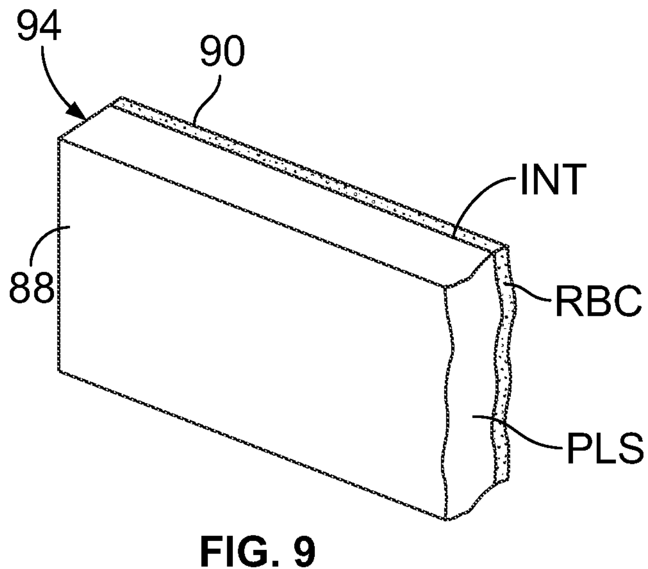
FIG. 9 is an enlarged perspective view of the channel of FIG. 7, with the interface being at an undesired low location within the channel.

As described above, the transition between the optically dense layer ABC and the less optically dense layer PLS may be referred to as the interface INT. The location of the interface INT within the channel 94 of the centrifugal separation chamber 36 can dynamically shift during blood processing, as FIGS. 7-9 show. If the location of the interface INT is too high (that is, if it is too close to the inner side wall portion 88 and the first outlet 102, as in FIG. 8), red blood cells can flow into the first outlet 102, potentially adversely affecting the quality of the low density components (platelet-rich plasma). On the other hand, if the location of the interface INT is too low (that is, if it resides too far away from the inner wall portion 88, as FIG. 9 shows), the collection efficiency of the system may be impaired. The ideal or target location of the interface INT may be experimentally determined, which may vary depending on any of a number of factors (e.g., the configuration of the centrifugal separation chamber 36, the rate at which the centrifugal separation chamber 36 is rotated about the rotational axis 38, etc.).

Figure 10:
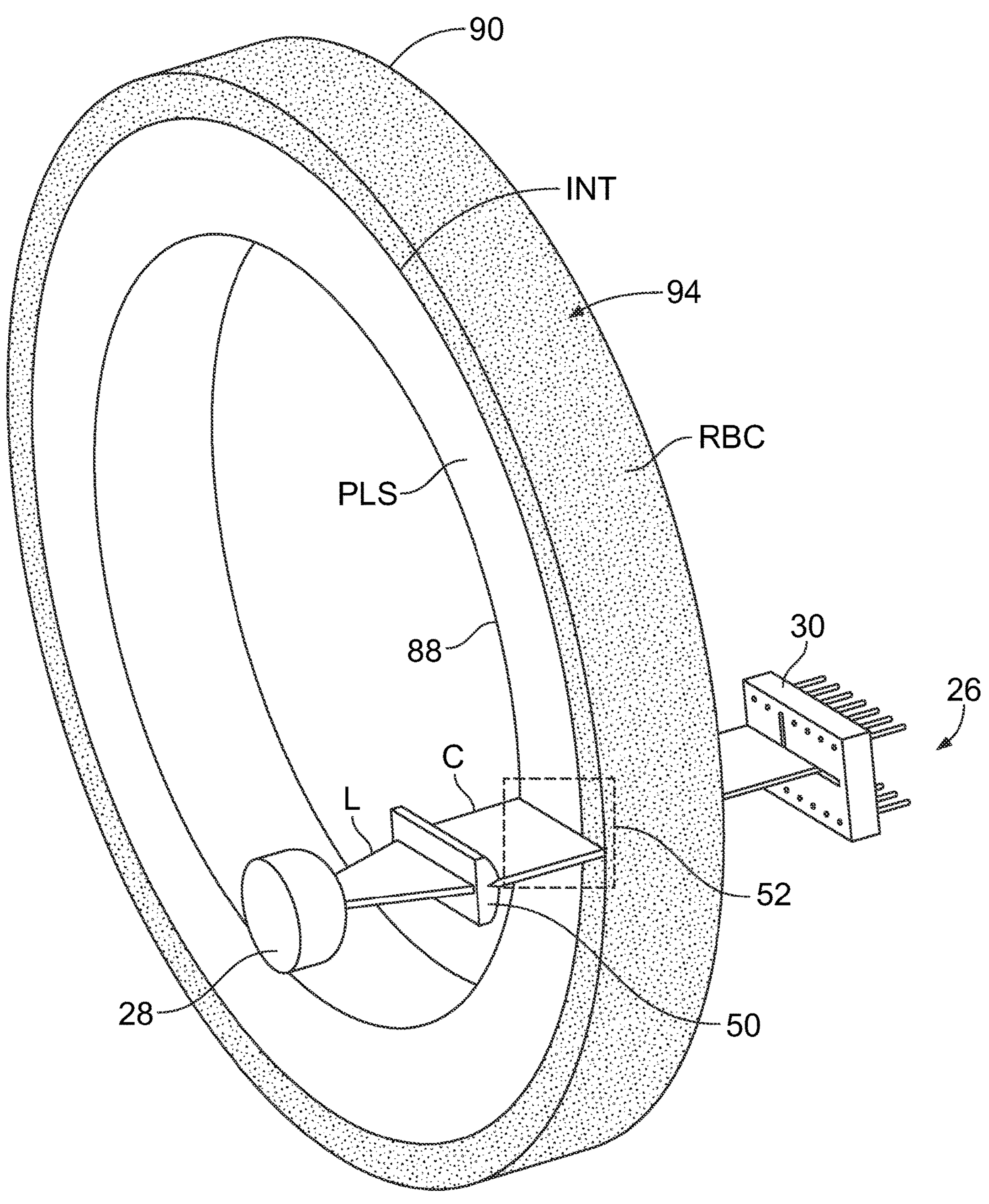
FIG. 10 is a diagrammatic view of a channel of the centrifugal separation chamber of FIGS. 5 and 6 and components of an exemplary interface monitoring assembly according to an aspect of the present disclosure.

As described above, the fluid separation device 10 may include an interface monitoring assembly 26 and a controller 18 with an interface control module to monitor and, as necessary, correct the location of the interface INT. FIG. 10 illustrates the components of an exemplary interface monitoring assembly 26, along with a simplified version of the channel 94 defined by the centrifugal separation chamber 36. The components of the interface monitoring assembly 26 include the light source 28 and light detector 30, along with a collimator 50. It should be understood that the interface monitoring assembly 26 may be provided with additional components (e.g., a light filter) without departing from the scope of the present disclosure.

As shown in FIG. 10, the light source 28, the light detector 30, and the collimator 50 are positioned in alignment with each other and with a monitored region 52 of the channel 94 in a direction substantially parallel to the rotational axis 38. As also shown in FIG. 10, the light source 28 and the collimator 50 are positioned on one side of the centrifugal separation chamber 36 (and its channel 94), while the light detector 30 is positioned on the opposite side. In one embodiment, the light source 28 and the collimator 50 are positioned on the same end of the centrifugal separation chamber 36 as the cover 93, with the light detector 30 positioned on the same end as the bottom 92 of the centrifugal separation chamber 36. In an alternative embodiment, the light source 28 and the collimator 50 are instead positioned on the same end of the centrifugal separation chamber 36 as the bottom 92, while the light detector 30 is positioned on the same end as the cover 93.

The components of the interface monitoring assembly 26 may be mounted to stationary surfaces of the centrifuge compartment 32 or may be configured to move with respect to stationary surfaces of the centrifuge compartment 32. If the components of the interface monitoring assembly 26 are mounted to stationary surfaces of the centrifuge compartment 32, they will always be in alignment and will monitor any portion of the channel 94 that rotates into alignment with the interface monitoring assembly 26 (provided that the associated portion of the centrifugal separation chamber 36 is formed of a light-transmissive material). If one or more of the components of the interface monitoring assembly 26 are mounted to movable components of the centrifugal separator 16, they may or may not remain in alignment with each other. For example, if all of the components of the interface monitoring assembly 26 are configured to rotate with the centrifugal separation chamber 36, they will remain in alignment with each other while monitoring only the portion of the channel 94 aligned with the interface monitoring assembly 26. On the other hand, if two or more of the components of the interface monitoring assembly 26 are configured to move with respect to each other (e.g., if the light source 28 and the collimator 50 are configured to rotate with the centrifugal separation chamber 36 while the light detector 30 is mounted to a stationary surface of the centrifuge compartment 32), then there will be times when the components of the interface monitoring assembly 26 are not aligned, such that light L from the light source 28 cannot reach the light detector 30. In this case, the interface monitoring assembly 26 will be able to monitor fluid within an aligned region of the channel 94 only when all of the components of the interface monitoring assembly 26 have moved into alignment with each other.

In any event, the light source 28 is oriented so as to direct light L toward the monitored region 52 of the channel 94, in a direction substantially parallel to the rotational axis 38. The configuration of the light source 28 may vary without departing from the scope of the present disclosure. For example, the light source 28 may be configured as a light-emitting diode or a laser. However, as will be described in greater detail herein, the light L is used to monitor the entire width of the monitored region 52 of the channel 94 (from the inner (low-g) wall portion 88 to the outer (high-g) wall portion 90), such that a less focused light L (e.g., the light from a light-emitting diode, rather than the light beam from a laser) may be advantageous. While FIG. 10 illustrates a single light source 28, it should be understood that a plurality of light sources may be employed without departing from the scope of the present disclosure. However, to reduce the effect of variability between the performance of two or more light sources, it may be advantageous to employ a single light source 28 to ensure that all light reaching the light detector 30 has come from a source having the same intensity.

In order to determine the location of the interface INT within the monitored region 52 of the channel 94, the light source 28 is configured to emit a light L having at least one wavelength that is substantially transmitted through one of the separated fluid components and substantially not transmitted through another separated fluid component (e.g., by being absorbed or reflected by the other separated fluid component). As the nature of fluids that may be separated and monitored within the centrifugal separation chamber 36 may vary, it should be understood that different types of light may be advantageous for monitoring different types of fluid. In the case of blood being separated into a packed red blood cell component RBC and a plasma component PLS, light L having a wavelength corresponding to red visible light (which may include red light or white light) is suitable for determining the location of the interface INT, as red light will be substantially transmitted through a plasma component PLS (and received by a properly positioned light detector 30) and substantially not transmitted through a red blood cell component RBC (and not received by the light detector 30).

As the light L is to be transmitted through the bottom 92 and cover 93 of the centrifugal separation chamber 36, at least the portions of the bottom 92 and cover 93 corresponding to the monitored region 52 of the channel 94 are formed of a material configured to transmit the light L (or at least the wavelength of the light L used to determine the location of the interface INT). While it is within the scope of the present disclosure for only a small portion of each of the bottom 92 and cover 93 of the centrifugal separation chamber 36 to be formed of a light-transmissive material, it may be advantageous for the entire bottom 92 and cover 93 (along with the entire centrifugal separation chamber 36) to be formed of the same light-transmissive material in order to simplify manufacture of the centrifugal separation chamber 36. It will, thus, be seen that the material composition of the bottom 92 and cover 93 of the centrifugal separation chamber 36 will determine the portion of the channel 94 that may be monitored by the interface monitoring assembly 26, as fluid in the channel 94 may only be monitored in locations where both the bottom 92 and cover 93 are formed of a light-transmissive material. Accordingly, if one or both of the bottom 92 and cover 93 are formed of a light-transmissive material at only one (aligned) location, only fluid within the channel 94 at that location will be monitored as it rotates into alignment with the interface monitoring assembly 26. Alternatively, if the entire bottom 92 and cover 93 are formed of a light-transmissive material, then fluid at any position within the channel 94 may be monitored as it rotates into alignment with the interface monitoring assembly 26 (in embodiments in which the centrifugal separation chamber 36 is rotatable with respect to the components of the interface monitoring assembly 26).

The collimator 50 is configured to receive at least a portion of the light L emitted by the light source 28 and direct the light L to the channel 94 as collimated light C. The collimated light C emitted from the collimator 50 (which may be configured as a collimating lens) extends along the width of the channel 94 (from the inner (low-g) wall portion 88 to the outer (high-g) wall portion 90), in generally parallel rays that are substantially parallel to the rotational axis 38.

The collimated light C emitted from the collimator 50 strikes the fluid in the channel 94 at a monitored region 52. If the collimator 50 is rotatable with the centrifugal separation chamber 36 or if the bottom 92 and the cover 93 are formed of light-transmissive material at only one aligned location, then only one portion of the channel 94 will ever be positioned at the monitored region 52. Alternatively, if the centrifugal separation chamber 36 is rotatable with respect to the collimator 50, each portion of the channel 94 will rotate into and out of the monitored region 52 (and be analyzed, if the associated portions of the bottom 92 and cover 93 of the centrifugal separation chamber 36 are formed of a light-transmissive material). According to another approach to defining the scope of the monitored region 52, the light source 28 may be controlled to be activated when a particular portion of the channel 94 is to be analyzed and deactivated when a portion of the channel 94 is not to be analyzed. Other approaches to defining the scope of the monitored region 52 may be employed without departing from the scope of the present disclosure.

If the interface monitoring assembly 26 is configured to analyze a monitored region 52 extending along only a portion of the length of the channel 94, the monitored region 52 may be positioned at any of a number of locations between the upstream and downstream ends of the channel 94. However, some locations of the channel 94 may be more advantageous to monitor than other locations. For example, while the simplified channel 94 of FIG. 10 shows an interface INT positioned at the same location along the entire length of the channel 94, it should be understood that the interface INT will be less discernable at the upstream end of the channel 94, where a fluid is first introduced into the channel 94 (and before it has been allowed to fully separate into multiple components). Thus, it may be advantageous to analyze a portion of the channel 94 positioned downstream of the upstream end of the channel 94 (e.g., midway between the upstream and downstream ends of the channel 94) for a more accurate indication of the location of the interface INT within the channel 94.

Turning now to the light detector 30, it is configured as an array of individual photodetectors. FIGS. 10-13 illustrate a light detector 30 configured as a linear or two-dimensional array, with a plurality of (preferably identical) individual photodetectors arranged in a line or row (or a two-dimensional space, in the case of a two-dimensional array). FIGS. 11A, 12A, and 13A (which will be described in greater detail) schematically illustrate the light detector 30 and the amount of collimated light C received by the individual photodetectors in the fluid flow conditions shown in FIGS. 11-13, respectively. A suitable light detector 30 may be of the type marketed by ams AG of Austria as the TSL1402R linear sensor array, though differently configured arrays may be employed without departing from the scope of the present disclosure. This may include the light detector 30 having any number of individual photodetectors (e.g., 256 photodetector elements), with a preference being for a greater number of smaller photodetectors (e.g., having a width on the order of one micrometer or less) for improved resolution.

Regardless of its exact configuration, the light detector 30 is configured and oriented such that at least one row of photodetectors extends along the width of the channel 94 (from the inner (low-g) wall portion 88 to the outer (high-g) wall portion 90) so as to be able to receive collimated light C exiting the channel 94 at any radial position within the monitored region 52. While it may be advantageous for the row of photodetectors to be arranged so as to coincide exactly with the width of the channel 94 in the monitored region 52, it is within the scope of the present disclosure for the row of photodetectors to have a width that is less than or greater than the width of the channel 94 in the monitored region 52.

As shown in FIGS. 10-13, the light detector 30 is aligned with and has the same orientation as the collimator 50, such that the light detector 30 is well-positioned to receive any collimated light C from the collimator 50 that is transmitted through the channel 94 of the centrifugal separation chamber 36 and any fluid therein. It may be advantageous for each of the collimator 50 and the row of photodetectors of the light detector 30 to be oriented along a radial line passing through the rotational axis 38, but it is within the scope of the present disclosure for them to be differently oriented. As described above, it is within the scope of the present disclosure for the light detector 30 and the collimator 50 to be movable with respect to each other, so it should be understood that the arrangement shown in FIGS. 10-13 represents the relative positions of the light detector 30 and the collimator 50 when they are aligned, which may include them being permanently aligned or them being periodically aligned as one moves with respect to the other during a fluid separation procedure (e.g., via rotation along with a movable component of the centrifugal separator 16).

As for how the interface monitoring assembly 26 is used to determine the location of the interface INT within the channel 94 during fluid separation, collimated light C travels through a light-transmissive portion of the bottom 92 or cover 93 of the centrifugal separation chamber 36 to intersect the separated fluid components within the channel 94 in the monitored region 52. After passing through the channel 94 and the fluids in the channel 94, at least a portion of the collimated light C (i.e., the portion not absorbed or reflected by the fluids) exits the channel 94 and then the opposite end of the centrifugal separation chamber 36 (i.e., the bottom 92 if the collimated light C entered the centrifugal separation chamber 36 via the cover 93 or the cover 93 if the collimated light C instead entered the centrifugal separation chamber 36 via the bottom 92), The transmitted portion of the collimated light C continues along its path (substantially parallel to the rotational axis 38) and is received by the light detector 30.

Figure 11:
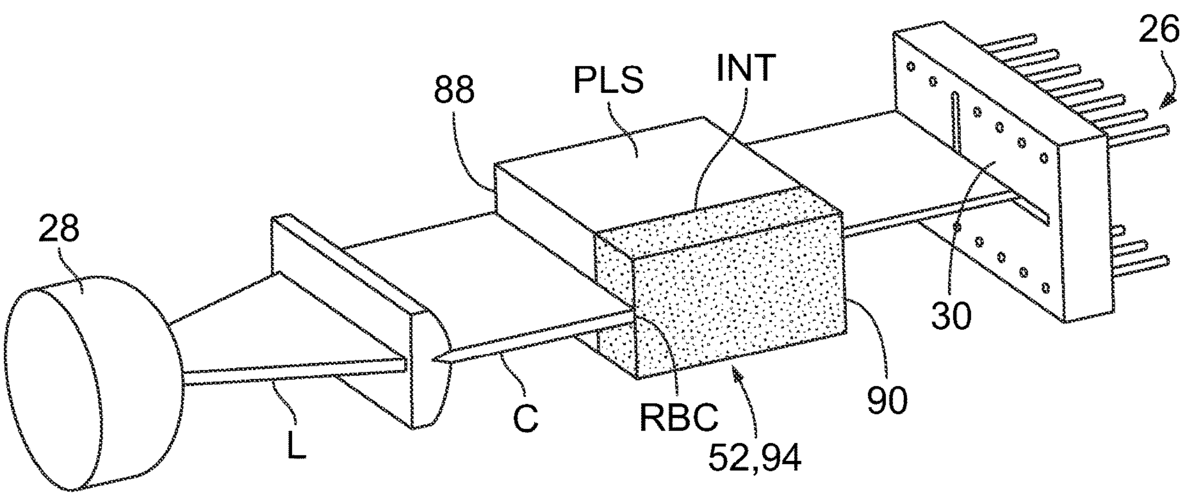
FIG. 11 is a diagrammatic view of the interface monitoring assembly and a monitored region of the channel of FIG. 10, with the interface between separated fluid components within the channel at an undesired low location.
Figure 11A:
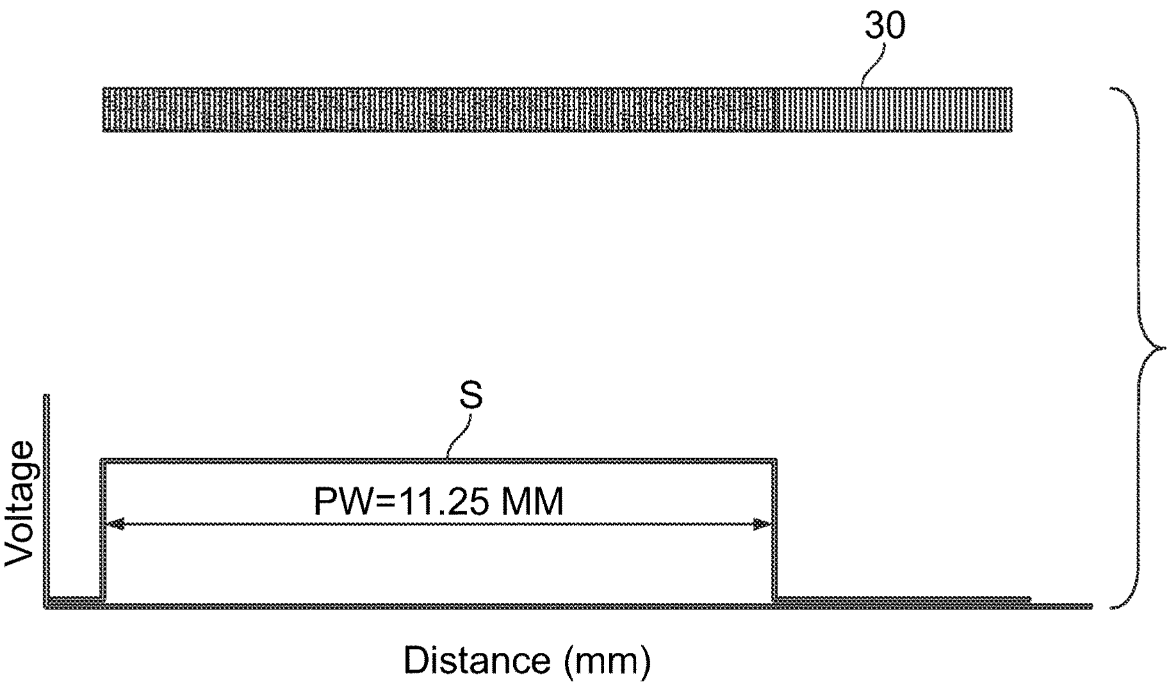
FIG. 11A is a diagrammatic view of the voltage output or signal transmitted by a light detector of the interface monitoring assembly of FIG. 10, during the fluid flow condition shown in FIG. 11.
Figure 12:
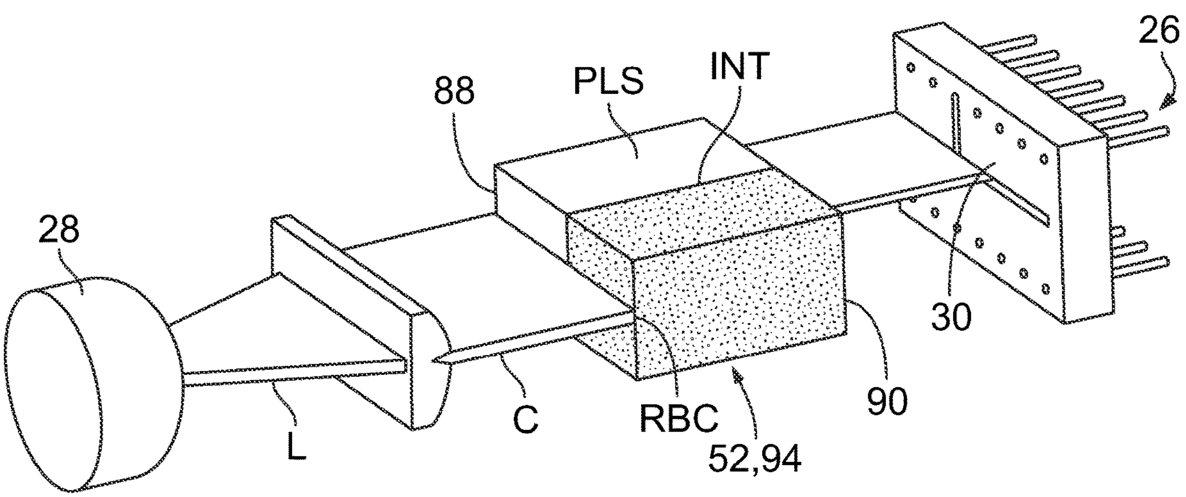
FIG. 12 is a diagrammatic view of the interface monitoring assembly and a monitored region of the channel of FIG. 10, with the interface between separated fluid components within the channel at a desired location.
Figure 12A:
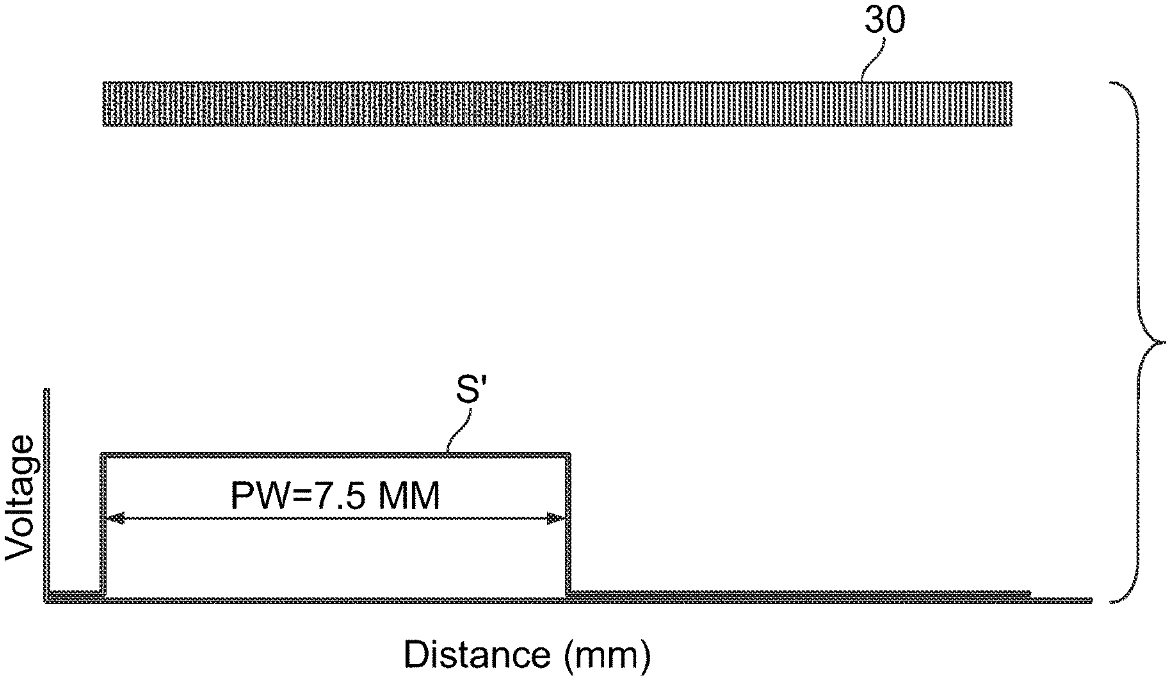
FIG. 12A is a diagrammatic view of the voltage output or signal transmitted by a light detector of the interface monitoring assembly of FIG. 12, during the fluid flow condition shown in FIG. 12.

Each individual photodetector will produce a signal having a voltage corresponding to the amount of collimated light C it has received, with FIGS. 11A and 12A illustrating the individual photodetectors that have received a greater amount of light (shown in FIGS. 11A and 12A as being shaded) and those that have received no light or a smaller amount of light (shown in FIGS. 11A and 12A as being unshaded) and the corresponding signals generated during the fluid flow conditions of FIGS. 11 and 12, respectively. In one embodiment, as described above, the light source 28 may be configured to emit a light L that is more readily transmitted by platelet-poor or platelet-rich plasma than by red blood cells, such as red visible light (from a light-emitting diode or a differently configured light source 28), which is substantially absorbed by red blood cells. Thus, a photodetector aligned with the plasma layer PLS within the monitored region 52 of the channel 94 will produce a signal having a relatively high voltage (due to receiving a relatively large amount of collimated light C), while a photodetector aligned with the red blood cell layer RBC within the monitored region 52 of the channel 94 will produce a signal having a relatively low voltage or even zero voltage (due to receiving substantially no light or at least a much smaller amount of light than a photodetector aligned with the plasma layer PLS). Accordingly, while FIGS. 11A and 12A show certain photodetectors (namely, those aligned with the red blood cell layer RBC in the monitored region 52 of the channel 94) as receiving substantially no collimated light C and, thus, not producing a signal (which may be understood as a signal having a voltage of zero), it should be understood that photodetectors aligned with the red blood cell layer RBC may receive some light and, thus, generate a signal, although the resulting signal will have a voltage that is notably lower than the voltage of a signal produced by a photodetector aligned with the plasma layer PLS.

The signals of the individual photodetectors collectively define the signal S, S' transmitted from the light detector 30 to the interface control module of the controller 18, with the location of the interface INT being associated with the spatial distribution of the collimated light C received by the light detector 30. In particular, each photodetector aligned with the plasma layer PLS will emit a "high voltage" signal, while each photodetector aligned with the red blood cell layer RBC will emit a "low voltage" signal, as described above. The plasma layer PLS and the red blood cell layer RBC each occupy a certain percentage of the width of the monitored region 52 of the channel 94, such that the distance of the pulse width of the signal S, S' transmitted by the light detector 30 (corresponding to the number of photodetectors emitting a "high voltage" signal) will be directly proportional to (and, in some cases, equivalent to) the width of the plasma layer PLS in the monitored region 52 of the channel 94. With this information regarding the width or thickness of the plasma layer PLS, the interface control module of the controller 18 may determine the location of the interface INT within the channel 94.

By way of example, the fluid flow conditions of FIGS. 11 and 12 may be compared. It will be seen that, in the fluid flow condition of FIG. 12, the red blood cell layer ABC occupies a greater percentage of the width of the channel 94 in the monitored region 52, such that the signal S' emitted by the light detector 30 (when analyzing the fluid flow condition of FIG. 12 will be shorter or narrower than the signal S emitted by the light detector 30 when analyzing the fluid flow condition of FIG. 11. Indeed, the signal S' emitted by the light detector 30 has a pulse width of 7.5 mm when analyzing the fluid flow condition of FIG. 12 (as shown FIG. 12A), while the signal S emitted by the light detector 30 has a pulse width of 11.25 mm when analyzing the fluid flow condition of FIG. 11 (as shown in FIG. 11A), which is indicative of the interface INT being closer to the outer (high-g) wall portion 90 (i.e., a greater distance from the inner (low-g) wall portion 88) in the fluid flow condition of FIG. 11 than in the fluid flow condition of FIG. 12. It should be understood that the distance of the pulse width of the signal S, S' transmitted by the light detector 30 may be measured by any suitable metric or unit (e.g., being measured in terms of dots (as in dots per inch or "DPI") or the number of individual photodetectors receiving collimated light C that has passed through the centrifugal separation chamber 36), which is in contrast to conventional systems that are time-based and measure the duration of a signal emitted by a light detector to determine the location of an interface within a channel of a centrifugal separation chamber.

2. Exemplary Interface Correction Procedure

When the interface control module of the controller 18 has determined the location or radial position of the interface INT in the monitored region 52 of the channel 94, it may compare the detected location to a target location. Upon determining that the interface INT is spaced away from the target location, the controller 18 (or its interface control module) may control the appropriate components of the fluid separation device 10 (e.g., the pump system and/or the centrifugal separator 16) to move the interface INT toward and to the target location.

Figure 13:
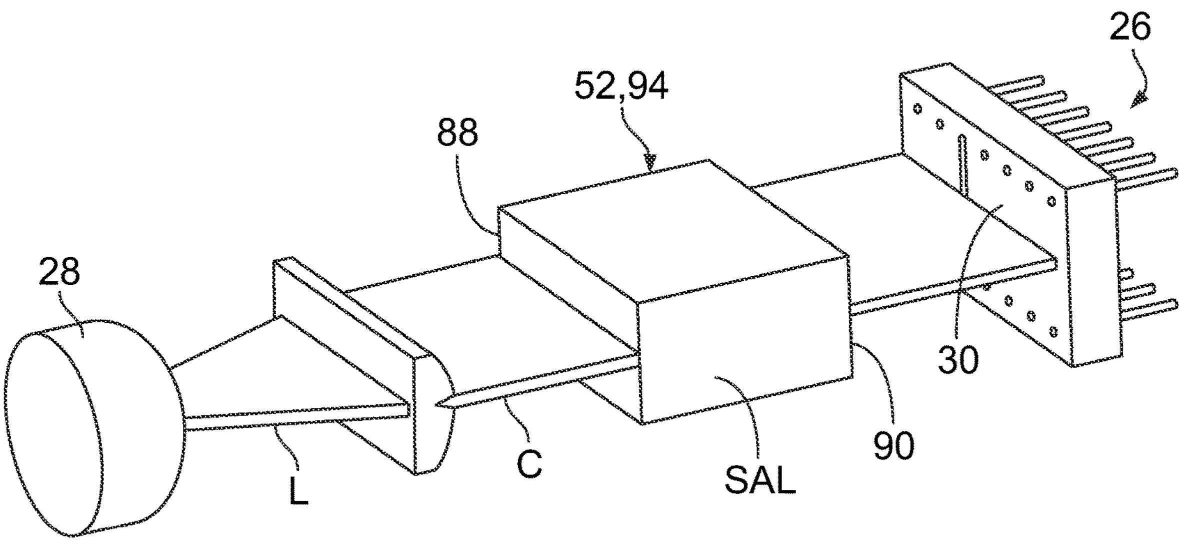
FIG. 13 is a diagrammatic view of the interface monitoring assembly and a monitored region of the channel of FIG. 10, with saline within the channel.
Figure 13A:
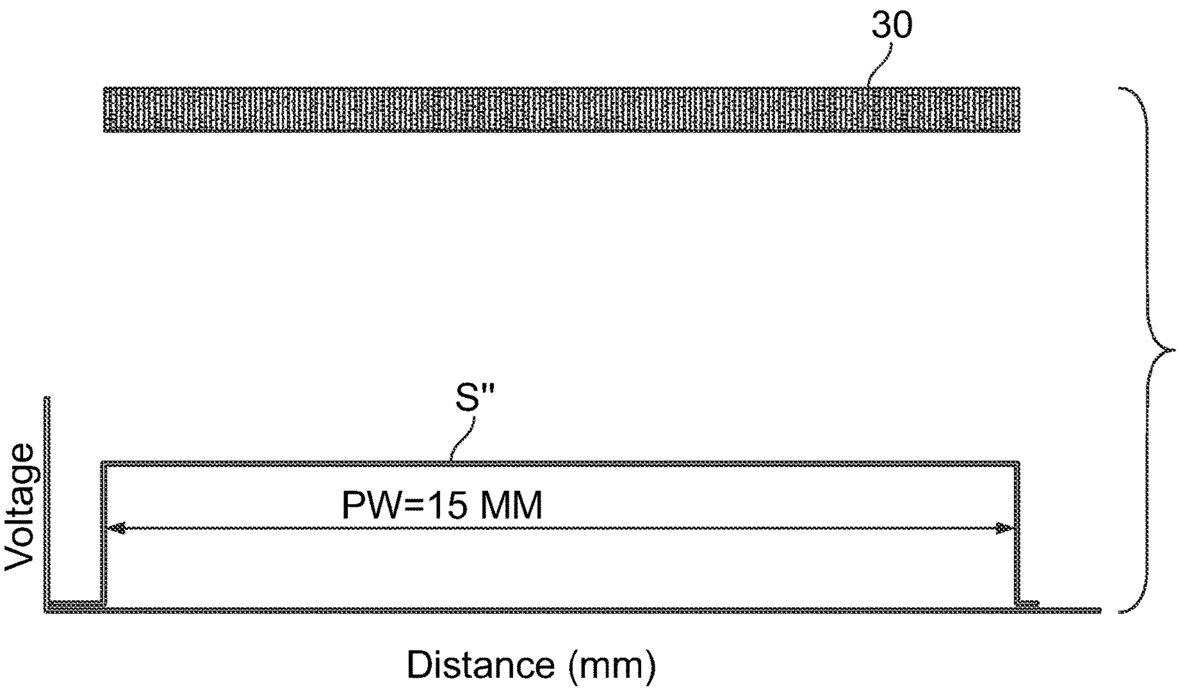
FIG. 13A is a diagrammatic view of the voltage output or signal transmitted by a light detector of the interface monitoring assembly of FIG. 10, during the fluid flow condition shown in FIG. 13.

According to an exemplary embodiment, interface control begins with a calibration phase that takes place before fluid separation has begun. During the calibration phase, the channel 94 is filled with a fluid that will transmit the collimated light C rather than absorbing or reflecting the light C or otherwise preventing the light C from reaching the photodetectors of the light detector 30. This fluid flow condition is illustrated in FIG. 13, with the calibration phase optionally taking place during a priming stage in which a light-transmissive priming fluid SAL (e.g., saline) is pumped through the channel 94 of the centrifugal separation chamber 36 (along with other regions of the fluid flow circuit 12) to move air from the fluid flow circuit 12 to a suitable location (e.g., into one of the containers F1-F5).

As shown in FIG. 13A, on account of all of the light C being transmitted through the channel 94, each of the photodetectors of the light detector 30 will receive a relatively large amount of light C and, thus, generate a "high voltage" signal. The distance of the pulse width of the signal S" transmitted by the light detector 30 during the calibration phase (which is shown as being 15 mm in FIG. 13A) will correspond to the entire width of the channel 94 in the monitored region 52. While not necessary, a calibration phase may be useful in ensuring the proper operation of the light source 28 and the light detector 30, standardizing the readings taken during a separation procedure in case of any irregularities or imperfections of the centrifugal separation chamber 36, and establishing a baseline value for the signal transmitted from the light detector 30 to the controller 18 when all of the components of the interface monitoring assembly 26 are aligned.

The controller 18 (or its interface control module) may compare the pulse width of a signal received during fluid separation (e.g., the signal S of FIG. 11A or the signal S' of FIG. 12A) to the pulse width of the signal S" generated during the calibration phase (FIG. 13A), which corresponds to the pulse width when light C is transmitted to the light detector 30 over the entire width of the channel 94 in the monitored region 52. The pulse width of the signal S" generated by the light detector 30 during the calibration phase may be referred to as the "calibration signal," while the signal S, S' generated during fluid separation may be referred to as the "current signal." Comparing these two pulse widths will indicate the percentage of the width of the channel 94 that is occupied by the plasma layer PLS and by the red blood cell layer RBC, which information may be used to determine the location of the interface INT within the channel 94. In particular, the interface position may be calculated as follows:

Interface position (%)=((calibration pulse width−current pulse width)/calibration pulse width)*100 [Equation 1]

It will be seen that Equation 1 effectively calculates the percentage of the width of the channel 94 in the monitored region 52 that is occupied by the red blood cell layer RBC, as the difference between the two pulse widths corresponds to the number of photodetectors of the light detector 30 that do not receive an elevated level of light C (and, thus, do not generate a "high voltage" signal) due to being aligned with the red blood cell layer RBC.

Figure 14:
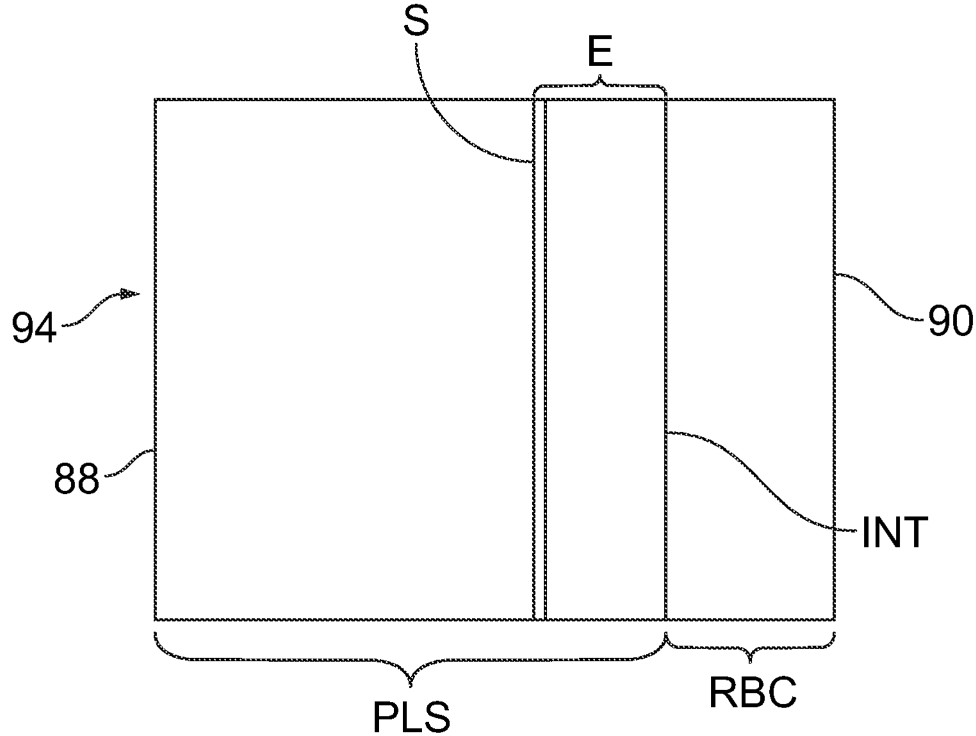
FIG. 14 is a diagrammatic view of the location of an interface between separated fluid components within a channel of the centrifugal separation chamber of FIGS. 5 and 6 compared to a target interface location.

When the location of the interface INT in the channel 94 has been determined, the controller 18 or its interface control module compares the actual interface location with the desired or target interface location, which may be referred to as the setpoint S. The difference between the setpoint S and the calculated interface position may be referred to as the error signal E, which is shown in FIG. 14. It should be understood that so expressing the error signal E in terms of a targeted red blood cell percentage value (i.e., the percentage of the width of the channel 94 that is actually occupied by the red blood cell layer RBC vs. the percentage of the width of the channel 94 that should be occupied by the red blood cell layer RBC) is merely exemplary, and that the error signal E may be expressed or calculated in any of a number of other ways.

In this exemplary embodiment, a negative error signal E indicates that the red blood cell layer RBC is too narrow in the monitored region 52 of the channel 94 (as FIGS. 11 and 14 show). The controller 18 or its interface control module generates a signal to adjust an operational parameter accordingly, such as by increasing the rate at which the plasma layer PLS is removed through the first outlet 102 under action of a pump of the fluid separation device 10. This causes the thickness or width of the plasma layer PLS to decrease, thus moving the interface INT toward and eventually to the target location (which is shown in FIG. 12), where the error signal E is zero. The controller 18 may repeatedly compare the calibration pulse width to the current pulse width during adjustment of the interface location to ensure that the interface INT reaches the target location.

On the other hand, a negative error signal E indicates that the width of the red blood cell layer RBC within the monitored region 52 of the channel 94 too large. In this case, the controller 18 or its interface control module generates a signal to adjust an operational parameter accordingly, such as by reducing the rate at which the plasma layer PLS is removed through the first outlet 102 under action of a pump of the fluid separation device 10. This causes the thickness or width of the plasma layer PLS to increase, thus moving interface INT toward and eventually to the target location, where the error signal E is zero. Once again, the controller 18 may repeatedly compare the calibration pulse width to the current pulse width during adjustment of the interface location to ensure that the interface INT reaches the target location.

It should be understood that this approach to controlling the location of the interface INT is merely exemplary and that different approaches may be implemented by the interface monitoring assembly 26 and controller 18 without departing from the scope of the present disclosure.

Aspects

Aspect 1. An interface monitoring assembly for use in combination with a centrifugal separator configured to rotate a centrifugal separation chamber about a rotational axis, the interface monitoring assembly comprising: a light source configured to emit a light; a light detector configured as a photodetector array; and a collimator positioned between the light source and the light detector, wherein the collimator is configured to receive at least a portion of the light emitted by the light source and direct collimated light through a channel defined by a centrifugal separation chamber in a direction substantially parallel to the rotational axis, the light detector is configured to receive at least a portion of the collimated light exiting the channel of the centrifugal separation chamber in said direction substantially parallel to the rotational axis, and the light detector is configured to emit a signal indicative of a location of an interface between separated fluid components within the channel of the centrifugal separation chamber.

Aspect 2. The interface monitoring assembly of Aspect 1, wherein the light detector is configured as a linear array of photodetectors.

Aspect 3. The interface monitoring assembly of Aspect 1, wherein the light detector is configured as a two-dimensional array of photodetectors.

Aspect 4. The interface monitoring assembly of any one of the preceding Aspects, wherein the collimator is configured as a collimating lens.

Aspect 5. The interface monitoring assembly of any one of the preceding Aspects, wherein the collimated light includes at least one wavelength of light configured to be substantially transmitted through a separated plasma component of whole blood within the channel of the centrifugal separation chamber and substantially not transmitted through a separated red blood cell component of the whole blood within the channel of the centrifugal separation chamber.

Aspect 6. The interface monitoring assembly of any one of the preceding Aspects, wherein the signal emitted by the light detector is based at least in part on a spatial distribution of the collimated light received by the light detector.

Aspect 7. A fluid separation device comprising: a centrifugal separator; a pump system; and a controller configured to control the pump system to convey fluid from a fluid source into a channel defined by a centrifugal separation chamber positioned within the centrifugal separator and to control the centrifugal separator to rotate the centrifugal separation chamber about a rotational axis so as separate at least a portion of the fluid in the channel of the centrifugal separation chamber, wherein the centrifugal separator includes an optical monitor assembly comprising a light source configured to emit a light, a light detector configured as a photodetector array, and a collimator positioned between the light source and the light detector, the collimator is configured to receive at least a portion of the light emitted by the light source and direct collimated light through the channel of the centrifugal separation chamber in a direction substantially parallel to the rotational axis, the light detector is configured to receive at least a portion of the collimated light exiting the channel of the centrifugal separation chamber in said direction substantially parallel to the rotational axis, the light detector is configured to emit a signal indicative of a location of an interface between separated fluid components within the channel of the centrifugal separation chamber, and the controller is configured to receive the signal from the light detector and determine the location of the interface between the separated fluid components within the channel of the centrifugal separation chamber based at least in part on the signal.

Aspect 8. The fluid separation device of Aspect 7, wherein the light detector is configured as a linear array of photodetectors.

Aspect 9. The fluid separation device of Aspect 7, wherein the light detector is configured as a two-dimensional array of photodetectors.

Aspect 10. The fluid separation device of any one of Aspects 7-9, wherein the collimator is configured as a collimating lens.

Aspect 11. The fluid separation device of any one of Aspects 7-10, wherein the collimated light includes at least one wavelength of light configured to be substantially transmitted through a separated plasma component of whole blood within the channel of the centrifugal separation chamber and substantially not transmitted through a separated red blood cell component of the whole blood within the channel of the centrifugal separation chamber.

Aspect 12. The fluid separation device of any one of Aspects 7-11, wherein the signal emitted by the light detector is based at least in part on a spatial distribution of the collimated light received by the light detector.

Aspect 13. The fluid separation device of any one of Aspects 7-12, wherein the controller is further configured to determine whether the interface is at a target location, and after determining that the interface is not at the target location, control the centrifugal separator and/or the pump system so as to cause the interface to move to the target location.

Aspect 14. A method for separating a fluid comprising: conveying fluid from a fluid source into a channel defined by a centrifugal separation chamber; rotating the centrifugal separation chamber about a rotational axis so as separate at least a portion of the fluid in the channel of the centrifugal separation chamber; emitting a light through a collimator; directing collimated light through the channel of the centrifugal separation chamber in a direction substantially parallel to the rotational axis; receiving at least a portion of the collimated light exiting the channel of the centrifugal separation chamber in said direction substantially parallel to the rotational axis; emitting a signal indicative of a location of an interface between separated fluid components within the channel of the centrifugal separation chamber; and determining the location of the interface between the separated fluid components within the channel of the centrifugal separation chamber based at least in part on the signal.

Aspect 15. The method of Aspect 14, wherein said at least a portion of the collimated light exiting the channel of the centrifugal separation chamber is received by a linear array of photodetectors.

Aspect 16. The method of Aspect 14, wherein said at least a portion of the collimated light exiting the channel of the centrifugal separation chamber is received by a two-dimensional array of photodetectors.

Aspect 17. The method of any one of Aspects 14-16, wherein the collimator is configured as a collimating lens.

Aspect 18. The method of any one of Aspects 14-17, wherein the collimated light includes at least one wavelength of light configured to be substantially transmitted through a separated plasma component of whole blood within the channel of the centrifugal separation chamber and substantially not transmitted through a separated red blood cell component of the whole blood within the channel of the centrifugal separation chamber.

Aspect 19. The method of any one of Aspects 14-18, wherein the signal is based at least in part on a spatial distribution of the collimated light exiting the channel of the centrifugal separation chamber.

Aspect 20. The method of any one of Aspects 14-19, further comprising determining whether the interface is at a target location, and after determining that the interface is not at the target location, causing the interface to move to the target location.

It will be understood that the embodiments and examples described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. An interface monitoring assembly for use in combination with a centrifugal separator configured to rotate a centrifugal separation chamber about a rotational axis, the interface monitoring assembly comprising:

a light source configured to emit a light;

a light detector configured as a photodetector array comprising a plurality of individual photodetectors; and a collimator positioned between the light source and the light detector, wherein the collimator is configured to receive at least a portion of the light emitted by the light source and direct collimated light through a channel defined by the centrifugal separation chamber in a direction substantially parallel to the rotational axis, the light detector is configured to receive at least a portion of the collimated light exiting the channel of the centrifugal separation chamber in said direction substantially parallel to the rotational axis, each photodetector of the light detector is configured to emit a signal having a voltage corresponding to an intensity of said at least a portion of the collimated light received by the photodetector, with the signals emitted by the photodetectors collectively defining a composite signal emitted by the light detector, and the composite signal has a pulse width corresponding to a spatial distribution of the photodetectors of the light detector emitting signals having a voltage greater than a minimum value, with the pulse width of the composite signal being indicative of a location of an interface between separated fluid components within the channel of the centrifugal separation chamber.

2. The interface monitoring assembly of claim 1, wherein the light detector is configured as a linear array of photodetectors.

3. The interface monitoring assembly of claim 1, wherein the light detector is configured as a two-dimensional array of photodetectors.

4. The interface monitoring assembly of claim 1, wherein the collimator is configured as a collimating lens.

5. The interface monitoring assembly of claim 1, wherein the collimated light includes at least one wavelength of light configured to be substantially transmitted through a separated plasma component of whole blood within the channel of the centrifugal separation chamber and substantially not transmitted through a separated red blood cell component of the whole blood within the channel of the centrifugal separation chamber.

6. A fluid separation device comprising:

a centrifugal separator;

a pump system; and a controller configured to control the pump system to convey fluid from a fluid source into a channel defined by a centrifugal separation chamber positioned within the centrifugal separator and to control the centrifugal separator to rotate the centrifugal separation chamber about a rotational axis so as separate at least a portion of the fluid in the channel of the centrifugal separation chamber, wherein the centrifugal separator includes an optical monitor assembly comprising a light source configured to emit a light, a light detector configured as a photodetector array comprising a plurality of individual photodetectors, and a collimator positioned between the light source and the light detector, the collimator is configured to receive at least a portion of the light emitted by the light source and direct collimated light through the channel of the centrifugal separation chamber in a direction substantially parallel to the rotational axis, the light detector is configured to receive at least a portion of the collimated light exiting the channel of the centrifugal separation chamber in said direction substantially parallel to the rotational axis, each photodetector of the light detector is configured to emit a signal having a voltage corresponding to an intensity of said at least a portion of the collimated light received by the photodetector, with the signals emitted by the photodetectors collectively defining a composite signal emitted by the light detector, the composite signal has a pulse width corresponding to a spatial distribution of the photodetectors of the light detector emitting signals having a voltage greater than a minimum value, with the pulse width of the composite signal being indicative of a location of an interface between separated fluid components within the channel of the centrifugal separation chamber, and the controller is configured to receive the composite signal from the light detector and determine the location of the interface between the separated fluid components within the channel of the centrifugal separation chamber based at least in part on the pulse width of the composite signal.

7. The fluid separation device of claim 6, wherein the light detector is configured as a linear array of photodetectors.

8. The fluid separation device of claim 6, wherein the light detector is configured as a two-dimensional array of photodetectors.

9. The fluid separation device of claim 6, wherein the collimator is configured as a collimating lens.

10. The fluid separation device of claim 6, wherein the collimated light includes at least one wavelength of light configured to be substantially transmitted through a separated plasma component of whole blood within the channel of the centrifugal separation chamber and substantially not transmitted through a separated red blood cell component of the whole blood within the channel of the centrifugal separation chamber.

11. The fluid separation device of claim 6, wherein the controller is further configured to determine whether the interface is at a target location, and after determining that the interface is not at the target location, control the centrifugal separator and/or the pump system so as to cause the interface to move to the target location.

12. A method for separating a fluid comprising:

conveying fluid from a fluid source into a channel defined by a centrifugal separation chamber;

rotating the centrifugal separation chamber about a rotational axis so as separate at least a portion of the fluid in the channel of the centrifugal separation chamber;

emitting a light through a collimator;

directing collimated light through the channel of the centrifugal separation chamber in a direction substantially parallel to the rotational axis;

receiving with a plurality of individual photodetectors at least a portion of the collimated light exiting the channel of the centrifugal separation chamber in said direction substantially parallel to the rotational axis;

emitting signals from the photodetectors as a composite signal having a pulse width corresponding to a spatial distribution of the photodetectors emitting signals having a voltage greater than a minimum value, with the voltage of each signal corresponding to an intensity of said at least a portion of the collimated light received by the photodetector and with the pulse width of the composite signal being indicative of a location of an interface between separated fluid components within the channel of the centrifugal separation chamber; and determining the location of the interface between the separated fluid components within the channel of the centrifugal separation chamber based at least in part on the pulse width of the composite signal.

13. The method of claim 12, wherein said at least a portion of the collimated light exiting the channel of the centrifugal separation chamber is received by a linear array of photodetectors.

14. The method of claim 12, wherein said at least a portion of the collimated light exiting the channel of the centrifugal separation chamber is received by a two-dimensional array of photodetectors.

15. The method of claim 12, wherein the collimator is configured as a collimating lens.

16. The method of claim 12, wherein the collimated light includes at least one wavelength of light configured to be substantially transmitted through a separated plasma component of whole blood within the channel of the centrifugal separation chamber and substantially not transmitted through a separated red blood cell component of the whole blood within the channel of the centrifugal separation chamber.

17. The method of claim 12, further comprising determining whether the interface is at a target location, and after determining that the interface is not at the target location, causing the interface to move to the target location.

* * * * *